(12) United States Patent
Pagi et al.

(10) Patent No.: US 11,996,196 B2
(45) Date of Patent: May 28, 2024

(54) INTELLIGENT COMPUTER APPLICATION FOR DIAGNOSIS SUGGESTION AND VALIDATION

(71) Applicant: CERNER INNOVATION, INC., Kansas City, KS (US)

(72) Inventors: Prashant Pagi, Karnataka (IN); Imran Shaikh, Karnataka (IN); Andrew Arun Kumar Boppuri, Karnataka (IN)

(73) Assignee: Cerner Innovation, Inc., Kansas City, MO (US)

( * ) Notice: Subject to any disclaimer, the term of this patent is extended or adjusted under 35 U.S.C. 154(b) by 298 days.

(21) Appl. No.: 17/107,150

(22) Filed: Nov. 30, 2020

(65) Prior Publication Data

US 2022/0172837 A1 Jun. 2, 2022

(51) Int. Cl.
*G16H 50/20* (2018.01)
*G16H 50/30* (2018.01)

(52) U.S. Cl.
CPC ............. *G16H 50/20* (2018.01); *G16H 50/30* (2018.01)

(58) Field of Classification Search
CPC ........ G16H 50/20; G16H 50/30; G16H 15/00; G16H 50/70; G06N 5/04; G06N 99/00; G06N 30/8693; G06F 18/217
USPC .......................................................... 705/2, 3
See application file for complete search history.

(56) References Cited

U.S. PATENT DOCUMENTS

| | | | |
|---|---|---|---|
| 2002/0107824 A1* | 8/2002 | Ahmed ................. | G16H 50/20 706/46 |
| 2005/0065813 A1* | 3/2005 | Mishelevich .......... | G16H 50/30 705/2 |
| 2009/0006129 A1* | 1/2009 | Thukral ................. | G16H 20/10 705/2 |
| 2011/0093481 A1* | 4/2011 | Hussam ................. | G16H 10/20 707/756 |
| 2015/0332283 A1* | 11/2015 | Witchey ................ | G16H 10/60 705/3 |
| 2016/0328526 A1* | 11/2016 | Park ....................... | G06N 20/20 |
| 2017/0270257 A1* | 9/2017 | St. Clair ................ | G16H 10/60 |
| 2017/0286622 A1* | 10/2017 | Cox ....................... | G16H 50/30 |
| 2017/0323064 A1* | 11/2017 | Bates ..................... | G16H 50/20 |

* cited by examiner

*Primary Examiner* — Alaaeldin M Elshaer
(74) *Attorney, Agent, or Firm* — Invoke

(57) ABSTRACT

In some examples, data associated one or more medical presentations of a person is received. A mapping that associates the data to one or more candidate diagnoses is determined. The one or more candidate diagnoses correspond to one or more possible medical conditions associated with the person. A validation score for a first candidate diagnosis, of the one or more candidate diagnoses, is generated based on a set of features associated with the person. The validation score indicates an accuracy of the candidate diagnosis. At least partially in response to the generating of the validation score, an indicator is caused to be provided at a user device. The indicator indicates the validation score.

25 Claims, 17 Drawing Sheets

| DIAGNOSIS | CC/RFV/SYMPTOMS/PROBLEMS [WEIGHTAGE] {DECISION FLAG} |
|---|---|
| CHOLELITHIASIS | SEVERE SUDDEN PAIN IN UPPER RIGHT ABDOMEN AND POSSIBLY EXTENDING TO UPPER BACK [4] {8} |
| | RIGHT UPPER QUADRANT PAIN [5] {8} |
| | NAUSEA WITH VOMITING, UNSPECIFIED [1] |
| | FEVER & SHIVERING [1] |
| | BROWN URINE [4] {8} |
| | CLAY COLORED STOOL [2] {8} |

*FIG. 4.*

| DIAGNOSIS | CC/RFV/SYMPTOMS/PROBLEMS [WEIGHTAGE] {DECISION FLAG} |
|---|---|
| OVARIAN CYST | LOWER ABDOMINAL PAIN [4] {11} |
| | PELVIC PAIN [5] {11} |
| | FULLNESS OR HEAVINESS IN YOUR ABDOMEN [2] {11} |
| | BLOATING [1] {11} |
| | PAIN WITH FEVER OR VOMITING [3] {11} |

DIAGNOSIS TO PRESENTING PROBLEM/CHIEF COMPLAINT/REASON FOR VISIT ASSOCIATION:

DIAGNOSIS LOOKUP:
○ DESCRIPTION  ● CODE

K80.0  [FIND]

DIAGNOSIS:
(K80.0) CHOLELITHIASIS (GALLBLADDER STONES)

MAPPED PRESENTING PROBLEM/CHIEF COMPLAINT/RFV:
- ABDOMINAL PAIN
- NAUSEA WITH VOMITING
- BROWN URINE
- CLAY COLORED STOOL
- RIGHT UPPER QUADRANT ABDOMINAL PAIN

[DELETE]

PRESENTING PROBLEM/CHIEF COMPLAINT/RFV LOOKUP:

PROBLEM TYPE: :CHIEF COMPLAINT/RFV:

TERMINOLOGY: [ ▼ ]   FIND:

PRESENTING PROBLEM/CHIEF COMPLAINT/REASON FOR VISIT:

| | |
|---|---|
| ABDOMINAL PAIN | PERIUMBILICAL PAIN |
| BELCHING BLOATING | POSTPRANDIAL PAIN |
| CLAY COLORED STOOL | RIGHT UPPER QUADRANT OF ABDOMEN |
| DIARRHEA, UNSPECIFIED | RIGHT UPPER QUADRANT PAIN |
| FUNCTIONAL DYSPEPSIA | STOMACH PAIN AROUND THE NAVEL AREA |
| FEVER, UNSPECIFIED | YELLOW SKIN OR EYES |
| HEARTBURN | NAUSEA WITH VOMITING |
| INDIGESTION | IRRITABLE BOWEL SYNDROME |
| IRRITABLE BOWEL SYNDROME | FEVER & SHIVERING |
| LOOSE/WATERY STOOLS | DYSPEPSIA |
| NAUSEA WITH VOMITING | DIARRHEA |
| PAIN IN YOUR RIGHT SHOULDER OR BACK | BROWN URINE |

[MAP]

[OK]  [CANCEL]

*FIG. 8.*

DIAGNOSIS TO PRESENTING PROBLEM/CHIEF COMPLAINT/REASON FOR VISIT ASSOCIATION:

DIAGNOSIS LOOKUP:
○ DESCRIPTION  ● CODE

R17  [FIND]

DIAGNOSIS:
(R17) JAUNDICE

MAPPED PRESENTING PROBLEM/CHIEF COMPLAINT/RFV:
- ABDOMINAL PAIN
- NAUSEA WITH VOMITING
- ANOREXIA
- LOSS OF APPETITE
- BROWN URINE
- YELLOW COLOR SKIN COLORED STOOL
- LEFT UPPER QUADRANT ABDOMINAL PAIN

[DELETE]

PRESENTING PROBLEM/CHIEF COMPLAINT/RFV LOOKUP:

PROBLEM TYPE: [CODIFIED PRESENTING PROBLEMS ▼]
TERMINOLOGY: [ ▼ ]   FIND: [ ]

PRESENTING PROBLEM/CHIEF COMPLAINT/REASON FOR VISIT:

| | |
|---|---|
| ABDOMINAL PAIN | PERIUMBILICAL PAIN |
| BELCHING BLOATING | POSTPRANDIAL PAIN |
| CLAY COLORED STOOL | RIGHT UPPER QUADRANT OF ABDOMEN |
| DIARRHEA, UNSPECIFIED | RIGHT UPPER QUADRANT PAIN |
| FUNCTIONAL DYSPEPSIA | STOMACH PAIN AROUND THE NAVEL AREA |
| FEVER, UNSPECIFIED | YELLOW SKIN OR EYES |
| HEARTBURN | NAUSEA WITH VOMITING |
| INDIGESTION | IRRITABLE BOWEL SYNDROME |
| IRRITABLE BOWEL SYNDROME | FEVER & SHIVERING |
| LOOSE/WATERY STOOLS | DYSPEPSIA |
| NAUSEA WITH VOMITING | DIARRHEA |
| PAIN IN YOUR RIGHT SHOULDER OR BACK | BROWN URINE |

[MAP]

[OK]  [CANCEL]

Figure 10A:
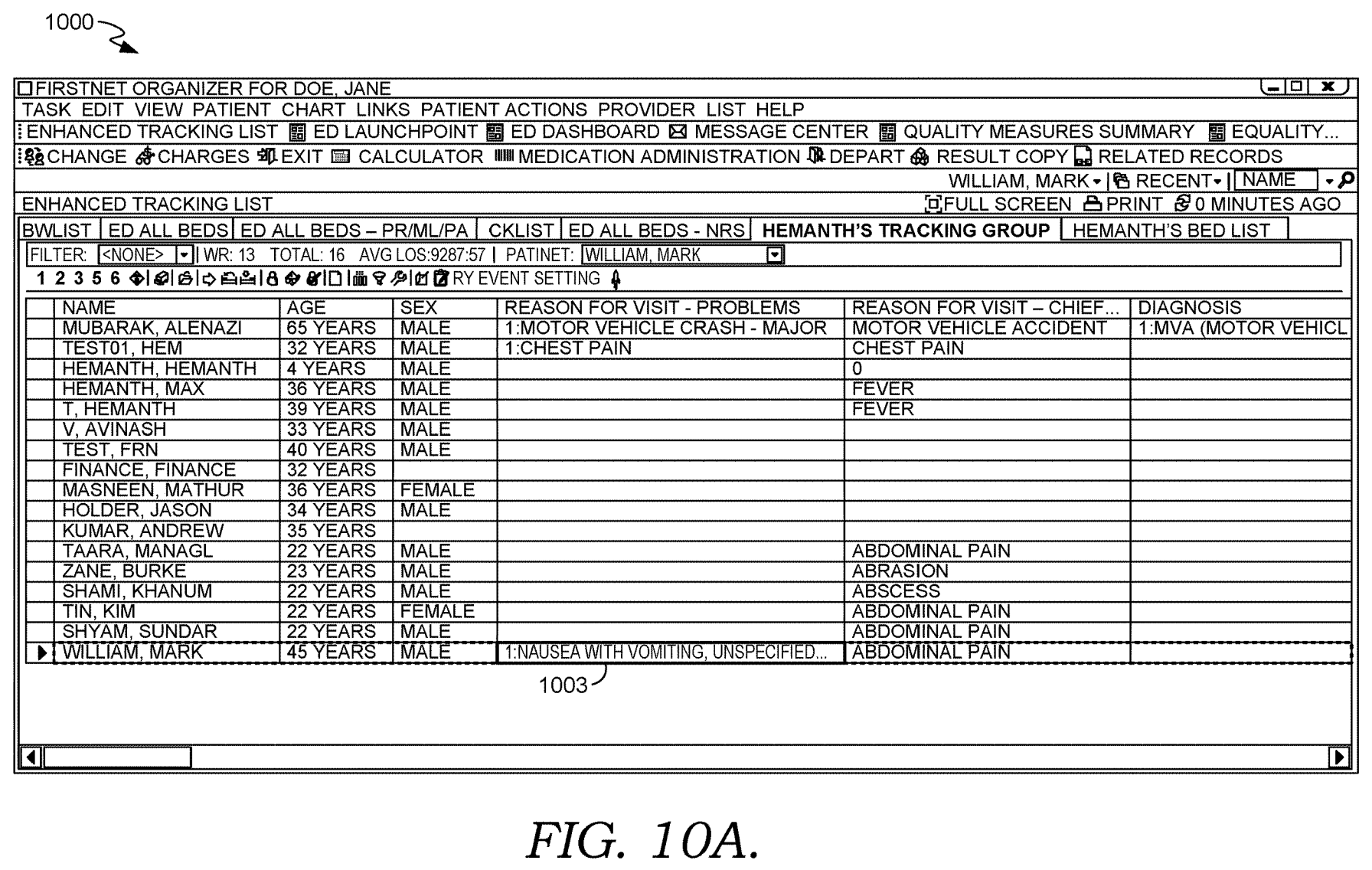

| NAME | AGE | SEX | REASON FOR VISIT – PROBLEMS | REASON FOR VISIT – CHIEF... | DIAGNOSIS |
|---|---|---|---|---|---|
| MUBARAK, ALENAZI | 65 YEARS | MALE | 1:MOTOR VEHICLE CRASH - MAJOR | MOTOR VEHICLE ACCIDENT | 1:MVA (MOTOR VEHICL |
| TEST01, HEM | 32 YEARS | MALE | 1:CHEST PAIN | CHEST PAIN | |
| HEMANTH, HEMANTH | 4 YEARS | MALE | | 0 | |
| HEMANTH, MAX | 36 YEARS | MALE | | FEVER | |
| T, HEMANTH | 39 YEARS | MALE | | FEVER | |
| V, AVINASH | 33 YEARS | MALE | | | |
| TEST, FRN | 40 YEARS | MALE | | | |
| FINANCE, FINANCE | 32 YEARS | MALE | | | |
| MASNEEN, MATHUR | 36 YEARS | FEMALE | | | |
| HOLDER, JASON | 34 YEARS | MALE | | | |
| KUMAR, ANDREW | 35 YEARS | MALE | | | |
| TAARA, MANAGL | 22 YEARS | MALE | | ABDOMINAL PAIN | |
| ZANE, BURKE | 23 YEARS | MALE | | ABRASION | |
| SHAMI, KHANUM | 22 YEARS | MALE | | ABSCESS | |
| TIN, KIM | 22 YEARS | FEMALE | | ABDOMINAL PAIN | |
| SHYAM, SUNDAR | 22 YEARS | MALE | 1:NAUSEA WITH VOMITING, UNSPECIFIED... | ABDOMINAL PAIN | |
| WILLIAM, MARK | 45 YEARS | MALE | | ABDOMINAL PAIN | |

DISCHARGE

DIAGNOSIS DEVIATION ALERT ◯ ← 1103

DIAGNOSIS (PROBLEM) BEING ADDRESSED THIS VISIT

+ ADD 🗒 MODIFY ⇆ CONVERT | DISPLAY: ALL ▾ | ⬚ 🔍 IMO

| CLINICAL DX | DATE | DX TYPE | CODE |
|---|---|---|---|
| ◯ CHOLELITHIASIS | 2/19/2020 | DISCHARGE | K80 |
| ⊙ UNSPECIFIED JAUNDICE | 2/19/2020 | DISCHARGE | R17 |

PROBLEMS

+ ADD 🗒 MODIFY ⇆ CONVERT ☐ NO CHRONIC PROBLEMS | DISPLAY: ACTIVE ▾ | 🔍 IMO

| NAME OF PROBLEM | ONSET DATE | CLASSIFICATION | QUALIFIER ▴ |
|---|---|---|---|
| ◯ NAUSEA WITH VOMITIN... | | DISCHARGE | K80 |
| ⊙ DARK BROWN URINE | 2/16/2020 | DISCHARGE | R17 |

[CLOSE]

*FIG. 11.*

INTELLIGENT COMPUTER APPLICATION FOR DIAGNOSIS SUGGESTION AND VALIDATION

BACKGROUND

Medical diagnosis is the process of predicting a medical condition, such as a particular disease, that a person has based on the person's symptoms (e.g., a pain description), the person's signs (e.g., vitals or gait pattern), or other medical presentations. When a diagnosis is accurate and made in a timely manner, a person has the best opportunity for a positive health outcome. However, when a diagnosis is inaccurate or not made in a timely manner, the person does not have as good of an opportunity for a positive outcome. Diagnostic errors (e.g., delayed, wrong, or incomplete diagnoses) are major contributors to negative patient outcomes, yet they remain a relatively understudied and unmeasured area of patient safety. Diagnostic errors have been shown to be associated with significantly high, but preventable, morbidity and mortality rates.

Computer-implemented technologies assist users (e.g., physicians) in diagnosing a person with a medical condition. However, such technologies lack accurate medical diagnosis functionality, thereby leading to diagnostic errors. Such technologies also employ arduous user interfaces or otherwise negatively affect the user experience, and lack intelligent automated functions, among other things. Further, these technologies are also deficient in terms of computing resource consumption.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to computer-implemented methods, computer storage media, and systems that can generate or analyze a mapping, such as one or more hash tables, that associates data to one or more candidate diagnoses. The associated data can be indicative of one or more medical presentations (e.g., symptoms, signs, chief complaint, etc.). This allows the one or more candidate diagnoses to be determined based on the one or more medical presentations. Some embodiments additionally generate a validation score for the one or more candidate diagnoses based on a set of features, where the validation score indicates an accuracy of the one or more candidate diagnoses that have already been determined. Such set of features can come from various attributes, such as the age of a person, gender of the person, medical history of the person, medical history of a family of the person, and social history of the person. This functionality improves existing technologies, as well as computer resource consumption, as described in more detail herein.

BRIEF DESCRIPTION OF THE SEVERAL VIEWS OF THE DRAWINGS

FIG. 4 illustrates an example table for suggesting one or more candidate diagnoses, according to some embodiments of the present invention;

FIG. 8 is a screenshot of an example user interface, according to some embodiments of the present invention;

FIG. 9 is a screenshot of an example user interface, according to some embodiments of the present invention;

FIG. 10A is a screenshot of an example user interface, according to some embodiments of the present invention;

FIG. 10B is a screenshot of an example user interface, according to some embodiments of the present invention;

FIG. 10C is a screenshot of an example user interface, according to some embodiments of the present invention;

FIG. 11 is a screenshot of an example user interface, according to some embodiments of the present invention;

DETAILED DESCRIPTION

Figure 1:
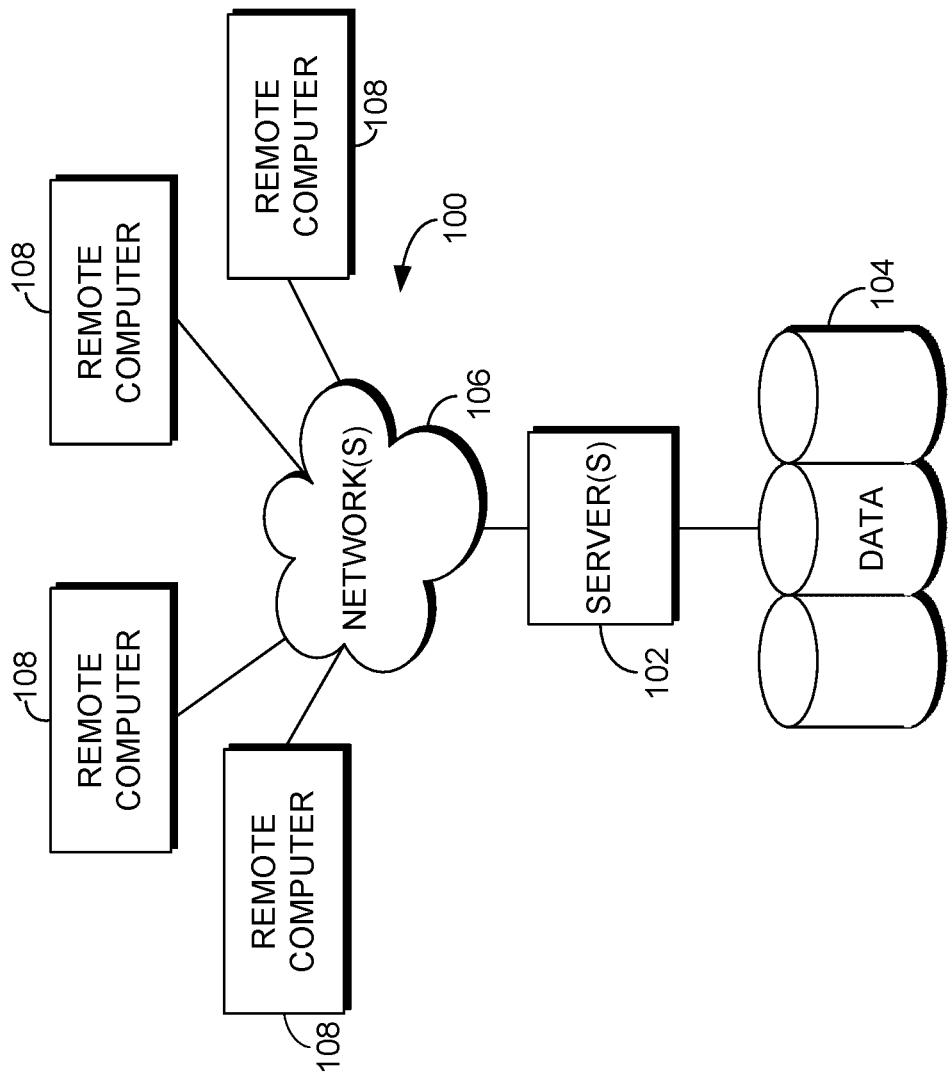
FIG. 1 is a block diagram of an example operating environment suitable to implement some embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

As stated above, existing computer-implemented technologies can assist users in diagnosing a person with a medical condition. However such technologies inaccurately predict medical diagnoses or fail to predict medical diagnoses at all. For example, technologies such as the IBM WATSON HEALTH computing system utilizes Artificial Intelligence (AI) and Natural Language Processing (NLP) to ingest and understand a corpus (e.g., Terabytes) of medical data to find patterns for medical diagnosis. However, these systems and other AI-based technologies still cannot understand or process medical jargon and fail to pick up on subtle clues that a human doctor, for example, would notice in medical presentation data. This is at least partly because these technologies tend to statically parse information and generate statistics and predictions about only basic outcomes of corpus data. However, reducing ingestion of a corpus source based on basic outcomes is problematic. For example, the information that physicians extract from a peer-reviewed article that they use to formulate a diagnosis may not be a major point of the article, yet these AI and NLP-based systems tend to completely disregard this information. Accordingly, this failure to adequately process medical presentation data causes useless and sometimes dangerous recommendations, leading to diagnostic errors.

In another example, existing computer application tools, such as electronic spreadsheet applications and other applications (e.g., PEPID), allow users to manually generate and associate medical presentations to a diagnosis. For example, an electronic spreadsheet, can store, in computer memory, manual user input in a field indicative of different symptoms a patient is experiencing and then store, in computer memory, other manual user input indicative of a diagnostic label that the user has associated with the symptoms. However, this requires arduous and extensive user input by listing out each symptom and label, thereby negatively affecting the user experience.

Relatedly, existing computer application tools have static user interfaces that require users to arduously drill down on, browse, or scroll through various pages to obtain relevant information. For example, existing computer tools have a page that is configured to store a list of all medical presentation inputs by a physician based on a medical examination. The physician typically has to then drill down to, scroll, or browse several other pages to match the stored list to medical presentations associated with suggested diagnoses. The physician may then yet again drill down, scroll, or browse other pages to ensure that the medication presentations are not indicative of other diagnoses so as to ensure a diagnostic error is not made. This tedious manual user activity is arduous and negatively affects the user experience.

These existing technologies and computers themselves are also deficient in terms of computing resource consumption, such as I/O, memory consumption, and network costs. For example, storing these redundant manual user inputs (e.g., medical presentation symptoms, medical diagnosis labels, and UI drilling) of existing technologies increases storage device I/O (e.g., excess physical read/write head movements on non-volatile disk) because each time a user inputs this information, the computing system may have to reach out to disk to perform a read or write operation for each user input, which is time consuming, error prone, and can eventually wear on components, such as a read/write head. This also increases memory consumption by having to store each manual user input. Such excessive memory storage also increases the likelihood of memory fragmentation, memory leaks, or other memory errors. In memory fragmentation instances, for example, these manual user inputs are not guaranteed to fit the memory heap in automated memory allocation and so there is a higher likelihood of unused memory or fragmentation.

Generating these redundant user inputs also causes excessive packet generation costs that adversely affect computer network communications, when using web applications, for example. Each time a user manually inputs information (e.g., medical symptoms and diagnosis) into a field and browses through or drills down various pages, for example, a request that includes payload data (e.g., a description of a symptom) and supplemental header information or other metadata within a packet in TCP/IP and other protocol networks must traverse over the network. Accordingly, for example, when this functionality is multiplied by all the user inputs, drilling, and browsing needed to obtain the desired diagnosis, there are network utilization and latency costs by repetitively generating this metadata, payload, and sending it over a computer network.

Various embodiments of the present disclosure are configured to provide technical solutions to these technical problems, among others, as described herein. In operation, particular embodiments of the present disclosure are directed to generating or analyzing a mapping (e.g., a hash table data structure) that associates data to one or more candidate diagnoses (e.g., a possible medical condition, such as a disease). Such data can be indicative of one or more medical presentations (e.g., symptoms, signs, chief complaint, etc.). This allows the one or more candidate diagnoses to be determined based on the one or more medical presentations. In some embodiments, such mapping is based on one or more predetermined rules. In an illustrative example, in response to a user, such as a physician, inputting patient's medical symptoms into a field on an app page, embodiments automatically map the medical symptoms to a disease through various conditional logic (a unique set of rules). In an illustrative example of such conditional logic, when embodiments check the gender of a patient (e.g., via the table 300 of FIG. 3) if the gender of the person is female, the logic checks for the age. If the age is >12, logic further checks the procedure history of the patient to see there is documentation for oophorectomy (removal of ovary). If there is no documentation of oophorectomy, various embodiments propose the candidate diagnosis as Ovarian Cyst. Such mapping or predetermined rules are configured to precisely guide the users to the correct candidate diagnosis.

Some embodiments of the present disclosure additionally generate a validation score for the one or more candidate diagnoses based on a set of features, where the validation score indicates an accuracy of the one or more candidate diagnoses that have already been determined. Such set of features can come from various rich attributes, such as the age of a person, gender of the person, medical history of the person, medical history of a family of the person, and social history of the person (e.g., whether the person smokes, drinks, etc.). In some embodiments, the generation of the validation score is configured to consider more features relative to the mapping or predetermined rules as described above, so as to provide a confirmation that the determination of the candidate diagnosis was correct.

In some embodiments, the validation score is generated by using the set of features as input into one or more machine learning models (e.g., a classifier model). In this way, hidden or otherwise latent weights can be learned to determine important features that would not otherwise be known based on hand-coding, predetermined rules, or conditional logic. For example, all of the training data together may indicate that the most prominent or important factor for a given diagnosis is age, even though no single training data source (e.g., a medical book) concludes that age is the most prominent factor.

In some embodiments, in response to the generation of the validation score, an indicator that indicates the validation score is generated and caused to be displayed to a user interface. These user interfaces, as described in more detail herein, are highly intuitive and easily navigable, especially via the automated functions described herein and the display of these indicators. In an illustrative example of these indicators, a green indicator may be displayed, which indicates that an original candidate diagnosis determination based on the mapping is maximally accurate. Alternatively, a yellow indicator may be displayed, which indicates that the original candidate determination based on the mapping is moderately accurate. Alternatively, a red indicator may be display, which indicates that the original candidate diagnosis based on the mapping is minimally or not very accurate.

Various embodiments of the present disclosure improve existing technologies, especially those described herein. As described above, technologies such as IBM WATSON HEALTH and other AI systems inaccurately predict medical diagnoses because they cannot understand or process medical jargon and fail to pick up on subtle clues that a human doctor, for example, would notice. However, the mapping functionality described herein to map data (e.g., via a data structure) to one or more candidate diagnosis based on one or more predetermined rules improves the accuracy. This is because these predetermined rules or conditional logic are configured to explicitly define or model subject matter experts (SME), such as doctors, and the way that they make medical diagnosis determinations. In other words, these subtle clues that existing AI systems do not pick up on are explicitly defined in the conditional logic or rules, thereby improving the accuracy of medical diagnosis. Further, the generation of the validation score alone improves the accuracy of medical diagnosis relative to other technologies because it gives an indication of an accuracy of any medical diagnosis determination.

Various embodiments of the present disclosure also improve existing technologies because they automate functionality based on a new set of rules that no existing technologies utilize. As described above, electronic spreadsheet applications and other applications (e.g., PEPID), allow users to manually generate and associate medical presentations to a diagnosis and doctors can manually check if the diagnosis is correct. However, this requires arduous and extensive user input by listing out each symptom and label, thereby negatively affecting the user experience. However, various embodiments automatically associate medical presentations to a diagnosis and validation using unique rules, thereby eliminating the need for arduous and extensive user input. For example, in response to receiving user input describing the signs/symptoms of a patient, various embodiments automatically map the signs/symptoms (e.g., via the predetermined rules described herein) to a candidate diagnosis and/or automatically generate an indicator indicating a validation score to a user interface. This eliminates the need for extensive manual user input and improves the user experience.

Various embodiments of the present disclosure improve existing user interfaces. As described above, existing computer application tools have static user interfaces that require users to arduously drill down on, browse, or scroll through various pages to obtain relevant information because of the tedious manual user activity that users must perform. However, various embodiments of the present disclosure do not require such drilling, scrolling, or browsing because they automate various functionality (e.g., the mapping and validation score) to a single page. In other words, for example, in response to a user inputting symptoms to a field on a page, embodiments can automatically map the symptoms to a candidate diagnosis and cause display of the candidate diagnosis on the same page and then cause display of the indicator indicating the validation score to the exact same page. Thus there is no need for additional drilling to other pages. Therefore, user navigation and the overall user experience is improved, as well as the user interfaces themselves.

Various embodiments of the present disclosure reduce computing resource consumption, such as I/O, memory consumption, and network costs. For example, because certain embodiments automatically map medical presentations to a candidate diagnosis and/or automatically generate a validation score, I/O is reduced because the computing system does not have to reach out to disk to perform a read or write operation for each manual user input. Memory consumption is also decreased because each manual user input does not have to be stored, thereby decreasing the likelihood of memory fragmentation, memory leaks, or other memory errors. In another example, such automation means that excessive packets are not being formulated and so the costs are lower so as to not adversely affect computer network communications, when using web applications, for example. By embodiments reducing the manual input, as well as the drilling, as described herein, payload data and supplemental header information or other metadata within a packet in TCP/IP and other protocol networks traverse over the network fewer times. Therefore, there are fewer network utilization and latency costs.

An exemplary computing environment 100 suitable for use in implementing embodiments of the present invention is described below. FIG. 1 is an exemplary computing environment (e.g., a medical-information computing-system environment) with which embodiments of the present invention may be implemented. The computing environment 100 is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other computing system environments or configurations. Examples of well-known computing systems, environments, and/or configurations that might be suitable for use with the present invention include personal computers, server computers, hand-held or laptop devices, wearable devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The computing environment 100 may correspond to a distributed computing environment where tasks are performed by remote processing devices that are linked through a communications network. In a distributed computing environment, program modules might be located in association with local and/or remote computer storage media (e.g., memory storage devices). Alternatively, the computing environment 100 represents client/server environments where In some embodiments, a user issues a query (or a command is issued) on a remote computer 108, after which the remote computer 108 communicates, via the network(s) 106, to the one or more servers 102 and the one or more servers 102 executes the query (e.g., via one or more components of FIG. 2) and causes or provides for display information back to the remote computer 108.

With continued reference to FIG. 1, the computing environment 100 comprises one or more computing devices in the form of server(s) 102. Exemplary components of the server(s) 102 comprise a processing unit, internal system memory, and a suitable system bus for coupling various system components, including data store 104, with the server(s) 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server(s) 102 typically includes therein, or has access to, a variety of computer-readable media. Computer-readable media can be any available media that might be accessed by server(s) 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by server 102. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The server(s) 102 might operate in one or more computer networks 106 using logical connections to one or more remote computers 108. Remote computers 108 might be located at a variety of locations in a medical or research environment, including clinical laboratories (e.g., molecular diagnostic laboratories), hospitals and other inpatient settings, ambulatory settings, medical billing and financial offices, hospital administration settings, home healthcare environments, clinicians' offices, Center for Disease Control, Centers for Medicare & Medicaid Services, World Health Organization, any governing body either foreign or domestic, Health Information Exchange, and any healthcare/government regulatory bodies not otherwise mentioned. Clinicians may comprise a treating physician or physicians; specialists such as intensivists, surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the server 102. The devices can be personal digital assistants or other like devices.

Computer network(s) 106 comprise a local area network (LANs) and/or a wide area network (WAN). Such networking environments are commonplace in offices, enterprise-wide computer networks, intranets, and the Internet. When utilized in a WAN networking environment, the server(s) 102 might comprise a modem or other means for establishing communications over the WAN, such as the Internet. In a networking environment, program modules or portions thereof might be stored in association with the server(s) 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., server(s) 102 and remote computers 108) might be utilized.

In operation, an organization might enter commands and information into the server(s) 102 or convey the commands and information to the server(s) 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the server(s) 102. In addition to a monitor, the server(s) 102 and/or remote computers 108 might comprise other peripheral output devices, such as speakers and a printer.

Although many other internal components of the server(s) 102 and the remote computers 108 are not shown, such components and their interconnection are well known. Accordingly, additional details concerning the internal construction of the server 102 and the remote computers 108 are not further disclosed herein, such as with respect to the computing device 1500 of FIG. 15. In some embodiments, the server(s) 102 represent a stand-alone computer or computing system, such as a mainframe, blade server, and the like. Alternatively, in some embodiments, the server(s) 102 represent a set of distributed computers, such as multiple cloud computing nodes where data is provisioned or exchanged between the cloud computing nodes.

Figure 2:
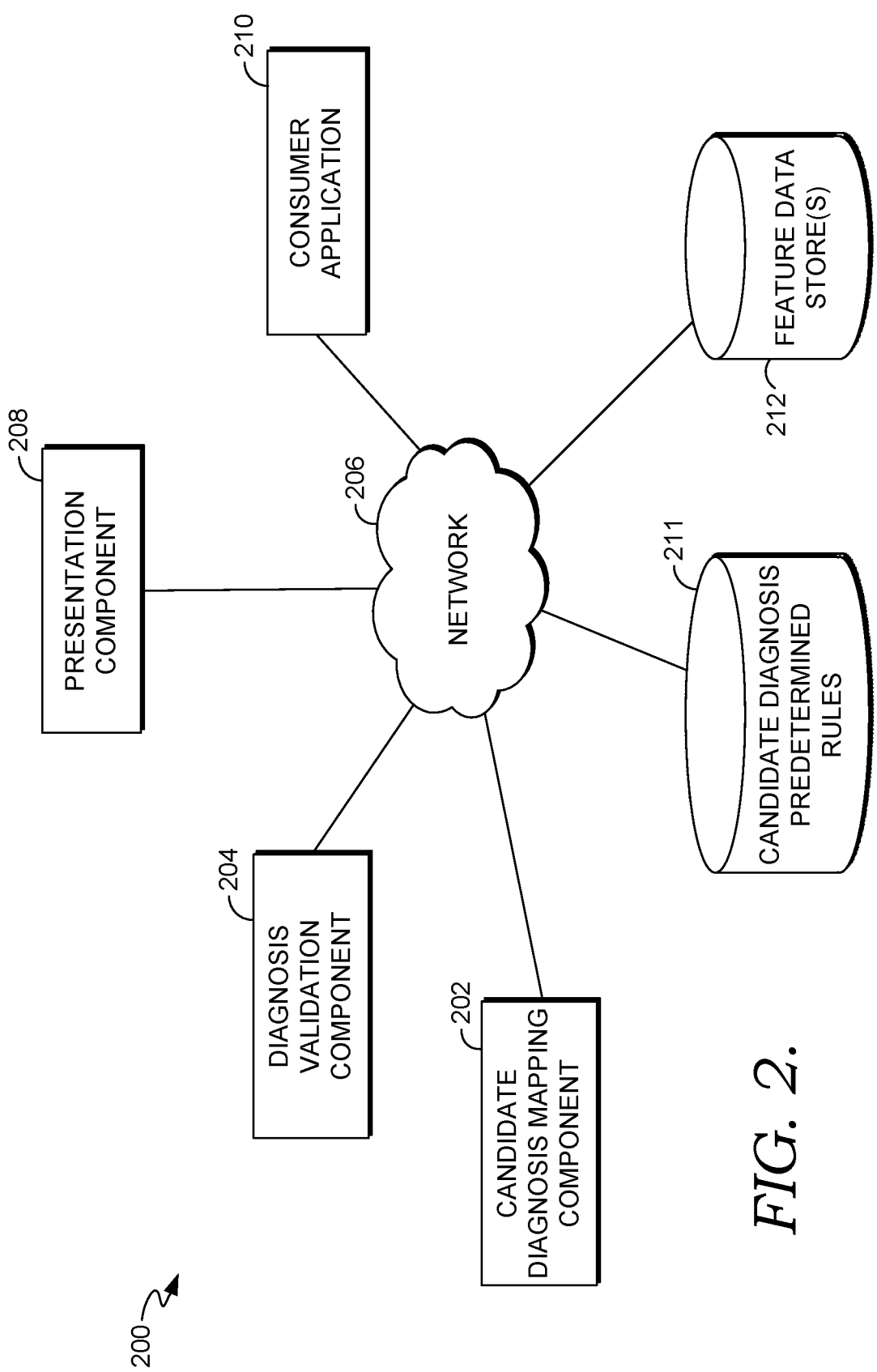
FIG. 2 illustrates an example computing system that is suitable for use in implementing some embodiments of the present invention.

Turning now to FIG. 2, an example computing system 200 is depicted suitable for use in implementing embodiments of the present invention. The computing system 200 is merely an example of one suitable computing system environment and is not intended to suggest any limitation as to the scope of use or functionality of embodiments of the present invention. Neither should the computing system 200 be interpreted as having any dependency or requirement related to any single module/component or combination of modules/components illustrated therein. In some embodiments, some or each of the computing system 200's components are located within the server(s) 102 of FIG. 1. Alternatively or additionally, in some embodiments, some or each of the computing system 200's components are located within the one or more remote computers 108.

In some embodiments, one or more of the illustrated components/modules of the system 200 may be implemented as stand-alone applications. In other embodiments, one or more of the illustrated components/modules may be distributed across multiple consult engines or computing device hosts. The components/modules illustrated in FIG. 2 are exemplary in nature and in number and should not be construed as limiting. Any number of components/modules may be employed to achieve the desired functionality within the scope of embodiments hereof.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The computing system 200 is generally configured to identify one or more candidate diagnoses of a person and generate a validation score that indicates an accuracy of the one or more candidate diagnoses, according to some embodiments. The system 200 includes the candidate diagnosis mapping component 202, the diagnosis validation component 204, the presentation component 208, the consumer application 210, the candidate diagnosis predetermined rule(s) 211, and the feature data store(s) 212, each of which are communicatively coupled via the network(s) 206. The network(s) 206 may include, without limitation, one or more secure local area networks (LANs) or wide area networks (WANs). In some embodiments, the network(s) 206 is a secure network associated with a facility such as a healthcare facility. In some embodiments, the secure network requires that a user log in and be authenticated in order to send and/or receive information over the network.

The candidate diagnosis mapping component 202 is generally responsible generating or analyzing a mapping that associates medical presentation data to one or more candidate diagnoses. Additionally or alternatively, the candidate diagnosis mapping component 202 is responsible for determining or identifying a candidate diagnosis (e.g., based on the mapping or a person's medical presentation data). A "mapping" as described herein refers to one or more data structures or data objects used to associate data. For example, a processor executing the candidate diagnosis mapping component 202 can read a hash table, lookup table, a knowledge graph structure, and/or other data structure for a field that lists all (or a threshold quantity of) medical presentation data that a user has provided and then responsively maps the field to a corresponding candidate diagnosis in a same record or entry as the list of medical presentation data. A "candidate diagnosis" as described herein refers to a candidate for a possible medical condition that a person has. In some embodiments, a candidate diagnosis is determined or identified based at least in part on the medical presentation(s) a user presents with, predetermined rules, and/or other features. A "medical condition" refers to a disease, disorder, disability, illness, sickness, and/or other health state that a person is in.

In some embodiments, the candidate diagnosis mapping component 202 uses one or more predetermined rules as stored in the data store 211 and/or a set of features stored to the feature data store(s) 212 to perform its mapping functionality. "Predetermined rules" as described herein refer to programmatic conditional statements, branch tests or pathways of tree data structures, and/or policies that have been stored to computer memory prior to receiving data that indicates one or more medical presentations of a person (or prior to receiving a request to identify one or more candidate diagnoses based on particular medical presentation(s) of the person). For example, a predetermined rule can be "if there is no documentation of Cholecystectomy for a patient, recommend a possible diagnosis as Cholelithiasis." Accordingly, in response to a request to identify a candidate diagnosis for the patient, some embodiments check if this rule is true.

The term "medical presentation," as described herein refers to a symptom of a person, a sign of a person, a chief complaint (CC) of a person, and/or a reason for visit (RFV) by a person. A "symptom" is what is subjectively described by a patient feeling the symptom. For example, a symptom of a common cold (e.g., the diagnosis) may be sinus pain from congestion or fatigue. A "sign" is objectively observed by a person, such as a healthcare practitioner (e.g., doctor or nurse), as opposed to what is felt by a person. For example, for the same common cold, a sign observed by a healthcare practitioner may be a runny nose. A "chief complaint" refers to one or more main or core symptoms or other problems that a person has complained of. For example, a patient's chief complaint may be a sore throat that is worse relative to other secondary complaints, such as watery eyes and stuffy nose. A "reason for visit" corresponds to a reason why a person is visiting a healthcare practitioner.

As indicated above, the candidate diagnosis mapping component 202 can use one or more predetermined rules as stored in the data store 211 and/or a set of features to perform its mapping functionality. In an illustrative example of this, a healthcare practitioner may input each medical presentation observed by a patient into a UI of an application (e.g., of the consumer application 210), as well as other feature values, such as gender, age, race, procedure history, social history, and/or family history of the patient. In response to receiving this input, the candidate diagnosis mapping component 202 can automatically map or associate each of these data to predetermined rules that govern what candidate diagnosis is selected given the rules and the medical presentation data. Examples of this are described in more detail below.

The diagnosis validation component 204 is generally responsible for generating one or more validation scores for one or more candidate diagnoses determined by the candidate diagnosis mapping component 202. A "validation score" indicates a degree or measurement of accuracy of a determined candidate diagnosis for one or more medical presentations. For example, in response to the candidate diagnosis mapping component 202 determining a candidate diagnosis based on symptoms a patient is experiencing and one or more predetermined rules, the diagnosis validation component 204 generates a validation score to determine how accurate the candidate diagnosis is.

In some embodiments, a "validation score" indicates a percentage or quantity of one or more recommended candidate diagnoses made by the candidate diagnosis mapping component 202 and the diagnosis validation component 204 that match for one or more given medical presentations. For instance, for each medical presentation of a person, the candidate diagnosis mapping component 202 may determine or associate the medical presentation with a candidate diagnosis. Likewise, the diagnosis validation component 205 can use each of the same medical presentations of a person and then determine or associate each of them to a candidate diagnosis (which may be the same or different relative to the determination made by the candidate diagnosis mapping component 202). Accordingly, the diagnosis validation component 204, in these embodiments, determines how many candidate diagnoses (that it determined) match (e.g., via a Jaccard index or other union function) other candidate diagnoses that the candidate diagnosis mapping component 202 performed, given the same medical presentation(s). In an illustrative example, for a first set of medical presentations of runny nose, sinus buildup, and headache, the candidate diagnosis mapping component 202 may have determined the candidates for each (or all) medical presentations to be "common cold" or "allergies." However, the diagnosis validation component 204 may determine that for the same medical presentations of runny nose, sinus buildup, and headache to be "common cold" only. Accordingly, there is a 50% match between the candidate diagnoses between the candidate diagnosis mapping component 202 and the diagnosis validation component 204 since "common cold" is included in both determinations but "allergies" is not.

In some embodiments, a validation score is not simply a confidence interval. A confidence interval (CI) is a range of values that is likely to include a population value within a certain degree of confidence. Confidence intervals thus take numerous random samples (from the same population) and calculate confidence intervals for each sample and a certain percentage of these ranges will contain a true population parameter or value (e.g., a probability that all members of the population will have the true value based on only testing a sample population). This certain percentage is a confidence interval. For example, confidence intervals can indicate that there is a 95% confidence or probability that a person's' medical symptoms are indicative of disease X based on various random samples of data in the features data sore(s) 212 sampled. This means that a computing system can be 95% confident that the population of all data in the data store(s) 212 (the entire population) falls in the range based on testing sub-samples of the entire population. Rather, some embodiments do not take random samples of data for the same population to make a prediction, but some embodiments verify the accuracy of a candidate diagnosis prediction based on additional features and/or methods (e.g., machine learning) of different populations relative to an original candidate diagnosis prediction. For example, in some embodiments, the candidate diagnosis mapping component 202 determines candidate diagnoses based only on the "sample" of data (a first population) in the candidate diagnosis predetermined rules stored in the data store 211. Further, in some embodiments, the diagnosis validation component 204 makes its predictions using at least some different data or features (a second population), such as is included in the feature data store(s) 212 corresponding to a different population relative to the data store 211.

In some embodiments, the generation of a validation score is not based on predetermined rules as indicated in the candidate diagnosis predetermined rule(s) 211 data store, but based on additional or other features as found in the feature data store(s) 212. The feature data store(s) 212 includes structured, semi-structured, and/or non-structured data, such as: medical charts of one or more persons or the person's family; social history information (e.g., alcohol, tobacco use) associated with one or more persons; age, gender, and/or race of one or more persons; peer-reviewed journals; medical news articles; medical books; medical blogs; social media pages of one or more persons, lab results of one or more persons, user device information (e.g., SMS text), sensor information (e.g., FITBIT or pulse oximeter readings) of one or more sensors that sample a user's medical condition, web or app pages from additional healthcare providers (e.g., pharmacy, physical therapy, optometrist, etc.), and/or any suitable data source that can be used to validate the determination made by the candidate diagnosis mapping component 202.

In some embodiments, the candidate diagnosis mapping component 202 and/or the diagnosis validation component 204 extracts and formats data within the feature data store(s) 212 using an Extract Transform Load (ETL) functionality. ETL refers to the concept of pulling (or copying) data from one or more source databases (e.g., a social media blog) and writing the pulled data into a target data store (e.g., a data warehouse or structured database). Specifically, for the "Extract" operation, data (e.g., raw data) is extracted or read from one or data sources (e.g., different web sources). For the "Transform" operation, the read data is converted from its previous form (e.g., raw form) into the form it needs to be in so that it can be placed in another database. Transform occurs by using lookup tables, one or more rules, or combining the read data with other data. In an illustrative example of the Transform operation, several unstructured data from social media services, blogs, patient charts, and the like can be joined to a single database table (or set of database tables), where keys or indexes are built so that records holding the data can be queried or retrieved based on a command. In another example, the Transform operation can additionally or alternatively clean, sort, validate, and/or prepare the read data. For the "Load" operation, the transformed data from the "Transform" operation is then written into a target data store. For example, using the illustration above, the stored single database table, keys, and indexes can be stored to a target database that can be queried or used via a command.

The diagnosis validation component 204 is configured to extract one or more features (e.g., natural language characters) from the feature data store(s) 212 (and/or the data store 211 and/or an ETL target data store) for further processing (e.g., via NLP). In some embodiments, some or each of these data sources (e.g., social media servers or other medical providers) in the feature data store(s) 212 employ particular Application Programming Interfaces (APIs) that are configured to communicate with the diagnosis validation component 204 by providing returning the relevant requested feature information, such as social media posts of a person, chart information of the person, and the like.

In some embodiments, the diagnosis validation component 204 is or uses one or more machine learning models to process the extracted features and generate the one or more validation scores. For example, the diagnosis validation component 204 can extract each feature, in natural language, from the feature data store(s) 212 and feed each feature to a classification-based learning model, which converts or encodes each natural language feature into one or more feature vectors, learns weights (e.g., via model training) associated with the one or more feature vectors, and then classifies whether the candidate diagnosis determined by the candidate diagnosis mapping component 202 is "maximally" accurate, "moderately" accurate, or "minimally" accurate. Machine learning functionality as it relates to various embodiments of the present disclosure is described in more detail herein.

In some embodiments, the validation score(s) produced by the diagnosis validation component 204 is a single score or prediction that indicates whether a candidate diagnosis is "accurate" or "not accurate." Alternatively or additionally, in some embodiments the validation score refers to a percentage or likelihood of accuracy (e.g., there is 83% likelihood that the original candidate diagnosis is correct). Alternatively or additionally, in some embodiments the validation score indicates whether a candidate diagnosis is "maximally accurate" over a first threshold, "moderately accurate" between a second threshold and the first threshold, and/or "minimally accurate" under the second threshold. For example, the first threshold may be greater than or equal to 70% such that the percentage of candidate diagnoses determined by the candidate diagnosis mapping component 202 that match equal to or greater than 70% of the candidate diagnoses as determined by the diagnosis validation component 204, for the same set of medical presentations, is determined to be "maximally" accurate (or a maximal match) Likewise, the percentage of candidate diagnoses determined by the candidate diagnosis mapping component 202 that match equal to or greater than between greater than or equal to 40% (e.g., the second threshold) and 70% (the first threshold) of the candidate diagnoses as determined by the diagnosis validation component 204, for the same set of medical presentations, is determined to be "moderately" accurate (or a moderate match). Likewise, the percentage of candidate diagnoses determined by the candidate diagnosis mapping component 202 that match equal to or less than 40% (below the second threshold) of the candidate diagnoses as determined by the diagnosis validation component 204, for the same set of medical presentations, is determined to be "minimally" accurate (or a minimal match).

Example system 200 also includes a presentation component 208 that is generally responsible for presenting content and related information to a user device (e.g., the remote computer 108), such as indicators that indicate the validation scores generated by the diagnosis validation component 204. In some embodiments, the presentation component 208 provides a user interface or other data based on the functionality of the candidate diagnosis mapping component 202 and/or the diagnosis validation component 204. Presentation component 208 may comprise one or more applications or services on a user device, across multiple user devices, or in the cloud. For example, in one embodiment, presentation component 208 manages the presentation of content to a user across multiple user devices associated with that user. Based on content logic, device features, and/or other user data, presentation component 208 may determine on which user device(s) content is presented, as well as the context of the presentation, such as how (or in what format and how much content, which can be dependent on the user device or context) it is presented, when it is presented. In particular, in some embodiments, presentation component 208 applies content logic to device features, or sensed user data to determine aspects of content presentation.

In some embodiments, the presentation component 208 generates, in near-real time (e.g., relative to the time at which embodiments receive data associated with medical presentation(s) of a person or relative to the time at which a user requests to identify a candidate diagnosis based on one or more medical presentations), one or more tags, flags, and/or otherwise structures data as output that is different than input data. For example, in response to a physician user inputting various data that describe medical presentations in a field (the input), the presentation component 208 can automatically format or tag each medical presentation (or a group of medical presentations) piece of data with an identifier that describes what the associated candidate diagnosis is (e.g., based on functionality performed by the candidate diagnosis mapping component 202 and/or the diagnosis validation component 204), which is the output. In various embodiments, these same flags, tags, formats, and/or output structure are the same regardless of the format of the application (e.g., the consumer application component or document that the user provides the input in.

In some embodiments, presentation component 208 generates user interface features associated with the candidate diagnosis mapping component 202 and/or the diagnosis validation component 204. Such features can include interface elements (such as graphics buttons, sliders, menus, audio prompts, alerts, alarms, vibrations, pop-up windows, notification-bar or status-bar items, in-app notifications, or other similar features for interfacing with a user), queries, and prompts. For example, the presentation component 208 can present: a validation score indicator (e.g., a colored graphic that indicates how accurate an original candidate diagnosis is for a given set of medical presentations), the mapping or determinations made by the candidate diagnosis mapping component 202, and/or any functionality performed by the diagnosis validation component 204.

Continuing with FIG. 2, example system 200 may include or operate in conjunction with one or more consumer applications 210. Consumer application 210 generally refers to one or more computer applications (e.g., stored to the remote computer 108) or services (e.g., stored to the server(s) 102), such as online/cloud applications or locally stored applications that consume or utilize components of the system 200. In some embodiments, the consumer application 210 includes web pages, app pages, UIs, activities, and/or other data formatted by the presentation component 208 of FIG. 2. In some embodiments, the consumer application 210 includes a field configured to receive user input of one or more medical presentations. In some embodiments, the consumer application 210 additionally or alternatively includes a field configured to provide (e.g., via the candidate diagnosis mapping component 202) one or more candidate diagnoses, given the inputted one or more medical presentations. In some embodiments, the consumer application 210 is configured to receive (e.g., via a user interface), a user selection of a first candidate diagnosis and responsively transmits (e.g., to the diagnosis validation component 204) an indication of the of user selection to compute a validation score. Examples of consumer applications 290 may include, without limitation, patient intake applications, medical chart applications, patient-centric medical diagnosis apps (used by patients not doctors), or other medical-related applications.

Figure 3:
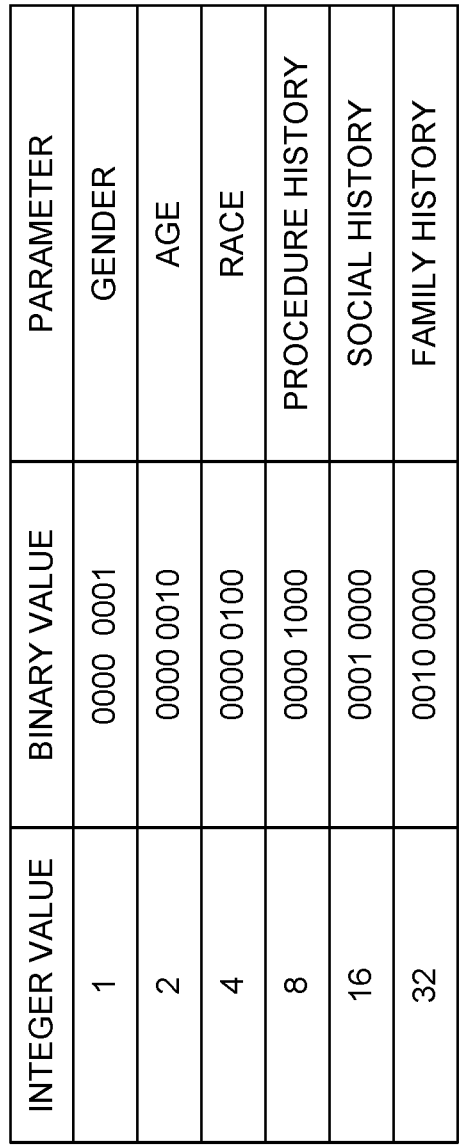
FIG. 3 illustrates an example table for suggesting a candidate diagnosis, according to some embodiments of the present invention.

FIG. 3 illustrates an example table 300 for suggesting a candidate diagnosis, according to some embodiments. In some embodiments, the table 300 at least partially illustrates what is stored to the candidate diagnosis predetermined rule(s) 211. In some embodiments, the table 300 at least partially illustrates the mapping analyzed and/or generated by the candidate diagnosis mapping component 202 of FIG. 2. In some embodiments, the table 300 illustrates a data structure, such as a hash table, a look-up table, or the like.

The table 300 illustrates multiple parameters (also referred to herein as features or attributes), such as gender, age, race, (or other demographic information, such as education, income, personal interests, etc.), procedure history, social history, and family history. "Procedure history" as described herein refers to a person's past medical history information, which can include information obtained from past medical surgeries, information obtained from past procedures, information obtained from past doctor's visits, information obtained from past medical consultations (e.g., via a telephone), information obtained from a patient's medical chart, and/or the like. For example, a procedure history can include all the dates a person has visited a doctor, the reason for the visit, the remedies prescribed by the physician, and the like.

"Social history," as described herein refers to any attribute of a person that addresses familial, occupational, and/or recreational aspects of a person's personal life that have the potential of being clinically significant. For example, social history can include whether a person smokes, whether the person drinks, whether the person takes particular medical or illicit drugs, the person's occupation, the person's diet, the amount of exercise the person gets, sexual behavior, the amount of travel, and/or the like. "Family history" as described herein refers to any medical conditions or other attributes known about family members (e.g., mother, father, siblings, grandparents, etc.) of a person. For example, for a first patient, the family history may include a prevalence of a particular type of cancer on the patient's paternal side of the family.

Each of these parameters in the table 300 are mapped to predetermined integer and binary values, each of which represent a decision making flag. A decision making flag is an indicator to determine a path or branch to take when making a determination for a candidate diagnosis. For example, if a patient presents with a first symptom, the candidate diagnosis may dependent on the patient's age. Accordingly, in some embodiments, in response to receiving a physician or other user inputting the first symptom into a computer application, a processor may read the binary value 0000 0010 (corresponding to integer value 2) corresponding to the patient's age to retrieve the patient's age. Responsive to this determination, embodiments determine a candidate diagnosis based at least in part on the person's age (as determined via this decision flag mapping).

In some embodiments, each medical presentation is assigned one of the pre-defined integer values illustrated in the table 300. In some embodiments, this decision-making flag logic is combined with a weight to determine a candidate diagnosis, as described in more detail below.

FIG. 4 illustrates an example table 400 for suggesting one or more candidate diagnoses, according to some embodiments. In some embodiments, the table 400 at least partially illustrates what is stored to the candidate diagnosis predetermined rule(s) 211 of FIG. 2. In some embodiments, the table 400 at least partially illustrates the mapping analyzed and/or generated by the candidate diagnosis mapping component 202 of FIG. 2. In some embodiments, the table 400 is combined or used with the table 300 of FIG. 3, as described in more detail below.

As described herein, some embodiments suggest or recommend a candidate diagnosis based on a pre-defined mapping between a diagnosis and one or more medical presentation data. In some embodiments, as illustrated in FIG. 4, each medical presentation data set is assigned a pre-defined weightage, ranging between 1 and 5, which are enclosed by square brackets. The higher the weigh value (i.e., the closer to 5 the value is), the closer is the candidate diagnosis or the more the particular medical presentation is indicative of a particular candidate diagnosis.

FIG. 4 indicates that a person or patient presents with medical presentations, as illustrated in the table 400 of FIG. 4 (e.g., "brown urine," "clay colored stool," etc.). In some embodiments, each medical presentation (e.g., CC) carries or is assigned a pre-defined weightage and a decision making flag (e.g., as described in FIG. 3), in order to determine a candidate diagnosis. Specifically, each decision flag is enclosed within a corresponding flower bracket (i.e., { }) and each weight is enclosed within a corresponding bracket (i.e., [ ]).

In some embodiments, for a given medical presentation or corresponding entry, a processor reads the value indicated in a given flower bracket and responsively reads the table 300 to check relevant parameters to make a decision before proposing a candidate diagnosis. For example, the entry 403 is read—"Right upper quadrant pain" and the weight [5] and the corresponding decision flag {8}. Responsively, embodiments locate the integer 8 or decision flag {8} within the table 300 of FIG. 3 and read the corresponding binary value, which indicates a rule to look-up the patient's procedure history before recommending a candidate diagnosis. In this way, for example, the integer 8 can act as a key within the table 300 such that the integer 8 in the square brackets of the table 800 can include a pointer value that points to the key value 8 within the table 300 so that the corresponding parameter can be read.

In various embodiments, such reading of the table 300 is indicative of inclusion or exclusion criteria. Inclusion criteria refers to parameters, attributes, or information that is included in an analysis for proposing or determining a candidate diagnosis given a set of medical presentations. For example, based on reading the entry 403, a processor can check, via the table 300, the procedure history of the patient to see if there is documentation (e.g., medical charts) indicating that the patient has undergone a Cholecystectomy (removal of gallbladder). In some embodiments, if there is no such documentation of Cholecystectomy, a processor proposes the possible diagnosis as Cholelithiasis (a first rule), as illustrated in the table 400 under the diagnosis column.

Exclusion criteria refers to parameters, attributes, or information that is included in an analysis for refraining from proposing a candidate diagnosis given a set of medical presentations. For example, using the illustration above, if there is documentation of cholecystectomy, certain embodiments refrain from proposing the possible diagnosis as Cholelithiasis, but proposes some other candidate diagnosis (e.g., a second rule).

In some embodiments, for each entry (or presentation symptom) of the table 400, a candidate diagnosis is generated based on the corresponding decision-making flag and weight of the given entry and a final weighting, summing, and/or voting occurs to determine the candidate diagnosis to propose. For instance, after each decision-making flag is read an a candidate diagnosis determined for each entry, each weight for the same candidate diagnosis determined for each entry can be added, multiplied, or otherwise linearly combined to formulate a final score, which is then compared with the final score for other candidate diagnoses made.

In an illustrative example, after reading the corresponding decision-making flags, the candidate diagnosis for the entries 401, 403, and 405 may be Cholelithiasis. However, the candidate diagnosis for the entries 407, 409, and 411 may be Cholecystitis (which is related but not the same). Responsive to determining the candidate diagnosis for each entry, embodiments may combine the weights for both Cholelithiasis and Cholecystitis. Since the combined weight for Cholelithiasis is higher, the candidate diagnosis is Choleliathiasis (and not Cholecystitis) for the aggregate medical presentations indicated in the table 400. Specifically, for example, the weight integers [5], [4], and [1] of the corresponding entries 401, 403, and 405 are added to arrive at a combined weight of 10 for Choleliathiasis. Likewise, the weight integers [1], [4], and [2] of the corresponding entries 407, 409, and 411 are added to arrive at a combined weight of 7 for Cholecystitis. Because the Choleliathiasis combined score of 10 is higher than the Cholecystitis combined score of 7, "Choleliathiasis" is chosen as the candidate diagnosis, as illustrated in the table 400. This indicates that there is a higher probability that Choleliathiasis is the correct diagnosis (relative to other diagnoses) given all the medical presentations inputted (i.e., each of the entries 401, 403, 405, 407, 409, and 411), even though some medical presentations may be indicative of multiple diagnoses or a different diagnosis.

In some embodiments, not every entry of the table 400 is read or considered for candidate diagnosis determinations but only those that have a weight value over a threshold regardless of what the decision-making flag is. For example the threshold may be an integer value of 2 and only those entries or medical presentations that have a weight value greater than or equal to 2 are considered. Accordingly, for example, only entries 401, 403, 409, and 411, are considered because each of the corresponding weight values are 2 or greater.

In some embodiments, each weight value (e.g., [5]) and decision making flag (e.g., {8}) are indicative of predetermined rules or policies. For example, a programmer may set the weight of [5] for right upper quadrant pain being indicative of Cholelithiasis and may set the decision-making flag to be {8} to check the procedure history. Such setting may occur in offline environments (non-runtime) or when a program is being built prior to a user inputting medical presentations as input based on a live or current healthcare visit. In some embodiments, such programming may utilize subject matter expertise (SME) or actual healthcare practitioner knowledge to define the weights and/or decision making flags. This predetermination or rule-setting is useful for health data, which can be complex, as described herein. As described above, existing technologies (e.g., IBM WATSON HEALTH) use little or no predetermined rules because the predictions are based on real-time data sampling via AI engines that are error prone because they tend to read (e.g., via NLP) resources incorrectly. Having predetermined rules ensures that there are no or relatively fewer processing errors compared to these technologies.

Figure 5:
FIG. 5 illustrates an example table for suggesting one or more candidate diagnoses, according to some embodiments of the present invention.

FIG. 5 illustrates an example table 500 for suggesting one or more candidate diagnoses, according to some embodiments. In some embodiments, the table 500 at least partially illustrates what is stored to the candidate diagnosis predetermined rule(s) 211 of FIG. 2. In some embodiments, the table 500 at least partially illustrates the mapping analyzed and/or generated by the candidate diagnosis mapping component 202 of FIG. 2. In some embodiments, the table 500 is combined or used with the table 300 of FIG. 3, as described in more detail below.

In some embodiments, the functionality used for the table 500 is identical to the functionality as described with respect to the table 400 of FIG. 4, except there have been different medical presentations inputted and therefore a different candidate diagnosis ("Ovarian Cyst") is recommended.

The table 500 illustrates that a person presents with the following medical presentations: lower abdominal pain, pelvic pain, fullness or heaviness in abdomen, bloating, and pain with fever or vomiting. The table 500 illustrates that "pelvic pain" has a weightage of [5] and the decision-making flag {11}. Accordingly, in response to reading the decision making flag {11}, some embodiments read the table 300 of FIG. 3 and specifically locate the corresponding decision making flag 11 within the table 300 of FIG. 3.

In some embodiments, some decision-making flag values are not directly located under the integer value column of the table 300. In these embodiments, a processor sums (or otherwise aggregates) one or more integer values (e.g., once) until arriving at the decision-making flag value to determine what parameters to look for. This is typically the case when there are more than one parameters within the table 300 that need to be checked. In an illustrative example, for the decision making flag {11}, there is no value of 11 under the integer value column of the table 300. Accordingly, some embodiments add integer value 8 (corresponding to "procedure history"), with integer value 2 (corresponding to "age"), and also add inter value 1 (corresponding to "gender"), which sums up to be the integer value 11. Accordingly, the integer value of 11 is a unique combination of gender (2)+age (1)+procedure history (8). This gives embodiments an indication to check the: age of the patient, the gender of the patient, and the procedure history of the patient. In this way, this logic acts as a type of "AND" gate functionality where the candidate diagnosis is only determined based on the age, gender, and procedure history of the patient being some "TRUE" or other value.

Examples of the inclusion criteria for the table 500 are indicated below. For example, when embodiments check the gender of a patient (e.g., via the table 300) if the gender of the person is female, the logic checks for the age. If the age is >12, embodiments further check the procedure history of the patient to see there is documentation for oophorectomy (removal of ovary). If there is no documentation of oophorectomy, various embodiments propose the candidate diagnosis as Ovarian Cyst, as illustrated under the "diagnosis" column of the table 500. This further illustrates that in some embodiments where a first attribute value (e.g., whether a patient has had an oophorectomy (e.g., a "TRUE" value)) is determined based on a second attribute value (e.g., the age of the person is greater than 12 (e.g., 15)).

Examples of the exclusion criteria for the table 500 are indicated below. If the gender of the person is male, some embodiments refrain from suggesting the probable or candidate diagnosis as Ovarian Cyst. If the gender of the person is female and the age is <12, particular embodiments refrain from suggesting the candidate diagnosis as Ovarian Cyst. If the gender is female and the age is >12, but the procedure history has Oophorectomy, particular embodiments refrain from suggesting the candidate diagnosis as Ovarian Cyst. In various embodiments, as described herein, the same logic is run against each entry or medical presentation of the table 400, before proposing a candidate diagnosis. Accordingly, in these embodiments, the decision-making flag methodology is applied on each documented medical presentation or entry on a scenario basis.

Figure 6:
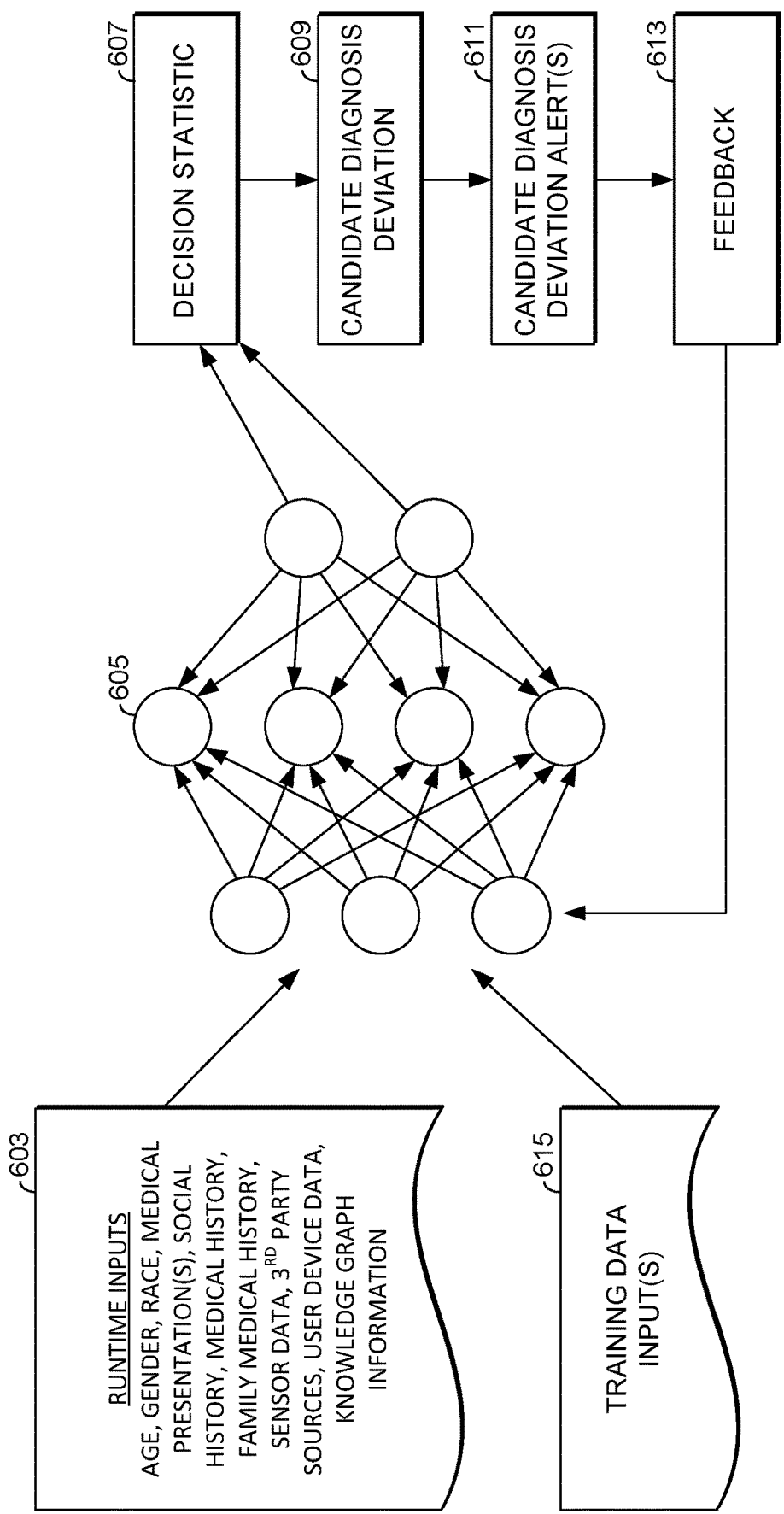
FIG. 6 is a schematic diagram illustrating how a validation score is generated using one or more machine learning models, according to some embodiments of the present invention.

FIG. 6 is a schematic diagram illustrating how a validation score is generated using one or more machine learning models, according to some embodiments. In some embodiments, FIG. 6 represents the data and functionality used by the diagnosis validation component 204 of FIG. 2. In some embodiments, the input(s) 603 represents what is stored to the feature data store(s) 212 of FIG. 2. In some embodiments, FIG. 6 represents functionality performed in response to a candidate diagnosis being determined via the tables 300, 400, and/or 500 of FIG. 3, FIG. 4, and FIG. 5 respectively.

FIG. 6 illustrates that one or more of the input(s) 603 are fed or processed through the machine learning model(s) 605 to predict the degree of accuracy (e.g., via candidate diagnosis deviation 609) with regard to a proposed candidate diagnosis (e.g., as determined by the candidate diagnosis mapping component 202 via the tables 300 and 400 of FIG. 3 and FIG. 4 respectively).

Although the input(s) 603 indicate specific inputs, they are representative only and more or fewer inputs may be used. In some embodiments, the phrase "medical history" includes procedure history of a person, diagnostic results of the person (e.g., lab and rad), such as lab results, X-rays, MRI results, etc., or other medical history. Sensor data refers to sensor readings associated with a person from any suitable device or sensor. For example, the sensor data can be sampled from a FITBIT (e.g., to measure the steps taken), a pulse oximeter to measure oxygen saturation levels, a sweat-sensing sensor to measure electrolytes, metabolites, and biomarkers, and/or any other suitable sensor. Third party sources correspond to any other remote information source (e.g., outside of a primary healthcare facility) that a primary entity can communicate with, over a computer network, to obtain suitable information. For example, third party sources can include a social media server, a pharmacological server, and the like that can be contacted for information regarding a person. In some embodiments, each of these third party sources have built in APIs so that a primary entity (e.g., a hospital) can communicate with these entities to obtain the desired information. User device data refers to any information that can be scraped or obtained from a user device (e.g., a mobile phone) of a person, such as texts, emails, pictures, and the like.

Knowledge graph information refers to any relationship information defined by a knowledge graph. For instance a knowledge graph can link each candidate medical diagnosis with each of its corresponding medical presentations. A "knowledge graph" or "network graph" is a pictorial representation or visualization for a set of objects where pairs of objects are connected by links or "edges." The interconnected objects are represented by points termed "vertices," and the links that connect the vertices are called "edges." Each node or vertex represents a particular position in a one-dimensional, two-dimensional, three-dimensional (or any other dimensions) space. A vertex is a point where one or more edges meet. An edge connects two vertices. In an illustrative example, a node may represent a diagnosis, and the node may be connected, via edges, to various other nodes representing each medical presentation associated with the diagnosis. These knowledge graphs help computers directly identify the relationships between different diagnoses and related medical presentations.

The one or more machine learning models 605 generates one or more particular decision statistic predictions 607 (e.g., a classification prediction of a classifier model, a clustering prediction of a clustering model, or a regression prediction for a regression model) given the runtime input(s) 603. Such machine learning model(s) 605 may be any suitable model of any suitable type. For example, such machine learning model(s) can be supervised or unsupervised and can be or include a neural network (e.g., a Convolutional Neural Network (CNN) or Siamese Neural Network), decision trees, random forests, support vector machine, Naïve Bayes, and or clustering (e.g., K-means clustering). Accordingly, although the machine learning model(s) 605 is represented as a neural network, it is understood that any suitable machine learning model (or combination of models) can alternatively or additionally be used. In an illustrative example of the decision statistic(s) 607, the machine learning model(s) 605 may cluster or classify a feature vector representing some or all of the input(s) 603 in a cluster or group representing a particular diagnosis.

In certain embodiments, the decision statistic(s) 607 may either be hard (e.g., membership of a class is a binary "yes" or "no") or soft (e.g., there is a probability or likelihood attached to the labels). Alternatively or additionally, transfer learning may occur. Transfer learning is the concept of re-utilizing a pre-trained model for a new related problem.

In some embodiments, the machine learning model(s) 605 converts or encodes the runtime input(s) 603 and/or training data input(s) 615 into corresponding feature vectors in feature space. A "feature vector" (also referred to as a "vector") as described herein includes one or more real numbers, such as a series of floating values or integers (e.g., [0, 1, 0, 0]) that represent one or more other real numbers, a natural language (e.g., English) word and/or other character sequence (e.g., a symbol (e.g., @, !, #), a phrase, and/or sentence, etc.). Such natural language words and/or character sequences correspond to the set of features and are encoded or converted into corresponding feature vectors so that computers can process the corresponding extracted features. For example, embodiments can parse, tokenize, and encode each natural language word within the runtime input(s) 603 into a single feature vector.

In various embodiments, the machine learning model(s) 605 learn, via training, parameters or weights so that similar features are closer (e.g., via Euclidian or Cosine distance) to each other in feature space. In some embodiments, this training is done in supervised manner using a loss function (e.g. Triplet loss or GE2E loss) that try to map similar features into one classification or cluster. Training can occur on any suitable training data input(s) 615, such as peer-reviewed journals, anonymized medical encyclopedias, medical textbooks, and the like. Some or each of these resources indicate whether particular age groups, medical presentations, social factors, sensor data, and the like are indicative of a particular diagnosis. Various embodiments can represent one or more feature vectors representing the input(s) 615 in vector space by aggregating (e.g. mean/median or dot product) the feature vector values to arrive at a particular point in feature space. For example, in supervised learning contexts, a training component can receive a training data source (e.g., a medical encyclopedia) and a specific label, such as "Ovarian Cyst" and the like that indicates that the attributes of the training data source is indicative of Ovarian Cyst. Embodiments, can then run the training data source with the corresponding labels through the machine learning model(s) 605 so that different feature values and weights are learned according to the label. In this way, when training data sources are received, corresponding weights or features can be learned.

In some embodiments, the training component of the machine learning model(s) 605 learns features from the training data input(s) 615 and responsively weights them during training. A "weight" in the context of machine learning represents the importance or significant of a feature or feature value for prediction. For example, each feature may be associated with an integer or other real number where the higher the real number, the more significant the feature is for its prediction. In some embodiments, a weight in a neural network or other machine learning application can represent the strength of a connection between nodes or neurons from one layer (an input) to the next layer (an output). A weight of 0 may mean that the input will not change the output, whereas a weight higher than 0 changes the output. The higher the value of the input or the closer the value is to 1, the more the output will change or increase. Likewise, there can be negative weights. Negative weights proportionately reduce the value of the output. For instance, the more the value of the input increases, the more the value of the output decreases. Negative weights may contribute to negative scores.

In another illustrative example of the training component, some embodiments learn an embedding of feature vectors based on learning (e.g., deep learning) to detect similar features between training data input(s) 615 in feature space using distance measures, such as cosine (or Euclidian) distance. For example, each labeled training data input 615 is converted from string or other form into a vector (e.g., a set of real numbers) where each value or set of values represents the individual features of the search result candidate or query in feature space. Feature space (or vector space) is a collection of feature vectors that are each oriented or embedded in space based on an aggregate similarity of features of the feature vector. Over various training stages or epochs, certain feature characteristics for each input(s) 615 can be learned or weighted. For example, for a first set of books that describe a first disease, the most prominent feature may be a first symptom, whereas other features change considerably or are not present, such as a second set of symptoms. Consequently, patterns of the first symptom can be weighted (e.g., a node connection is strengthened to a value close to 1), which is indicative of the label taking on this feature (whereas other node connections representing the second set of symptoms are weakened to a value closer to 0). In this way, embodiments learn weights corresponding to different features such that similar features found in inputs contribute positively for predictions.

In various embodiments, subsequent to the machine learning model(s) 605 training, the machine learning model(s) 605 (e.g., in a deployed state) receives the runtime input(s) 603. In various embodiments, the runtime input(s) 603 represents values associated with a patient for whom a candidate diagnosis has or will be made. For example, in some embodiments, in response to the candidate diagnosis mapping component 202 suggesting a candidate diagnosis (e.g., to a physician) given the set of medical presentations inputted at an application, embodiments can automatically query various data sources to obtain the runtime input(s) 603. Responsively, in some embodiments, the input(s) 603 are automatically converted to one or more feature vectors and mapped in the same feature space as vector(s) representing the training data input(s) 615. Responsively, some embodiments determine a distance (e.g., a Euclidian distance) between the one or more feature vectors and other vectors representing the training data input(s) 615, which is used to generate the decision statistic(s) 607. For example, a feature vector representing the values of the runtime input(s) 603 may be closest to a cluster of feature vectors representing an "Ovarian Cyst" diagnosis. Accordingly, in this example, the decision statistic 607 may be a prediction that the person associated with the runtime input(s) 603 has an Ovarian Cyst.

As illustrated in FIG. 6, the decision statistic(s) 607 is passed to the candidate diagnosis deviation 609 (e.g., the diagnosis validation component 204 of FIG. 2 or a sub-component of the diagnosis validation component 204). In some embodiments, the candidate diagnosis deviation 609 performs functionality to generate a validation score, as described herein. In some embodiments, the candidate diagnosis deviation functionality 609 compares the decision statistic(s) 607 with the candidate diagnos(es) (e.g., as determined by the candidate diagnosis mapping component 202 of FIG. 2) to determine whether there is a match between the decision statistic(s) 607 and the candidate diagnos(es) or determine how much the candidate diagnos (es) for each entry (e.g., the entry 403) deviates from the decision statistic 607.

In an illustrative example, referring back to FIG. 4, it can be determined that for the entries 401, 403, and 405, the suggested candidate diagnosis is Cholelithiasis. However, the candidate diagnosis for the entries 407, 409, and 411 may be Cholecystitis (which is related but not the same). Accordingly, for example, the candidate diagnosis deviation 609 functionality can determine whether there is a match between each decision statistic(s) 607 made for each of the corresponding entries or medical presentations relative to each candidate diagnosis suggestion. In this way, in some embodiments, a decision statistic 607 is generated for each entry and compared to each candidate diagnosis suggested for each of the corresponding entries in the table 400. For example, using the illustration above, for the entries 401, 403, and 405, the decision statistic 607 may be Cholelithiasis, Cholelithiasis, and Cholecystitis respectively, whereas for the entries 407, 409, and 411, the decision statistic may be Cholecystitis, Cholecystitis, and Cholecystitis respectively. In these embodiments, the candidate diagnosis deviation functionality 609 determines the overlap or matching (e.g., via Jaccard Index) for all entries for both the candidate diagnosis suggestion and the decision statistic(s) 607. In this example, there is an 83% match between all of the candidate diagnoses made for each entry and all of the decision statistic 607's made for the same entries. That is, only one candidate diagnosis determination is different for the entry 405 between an original candidate diagnosis and the decision statistic 607, whereas all the other candidate diagnosis determinations are the same for the other entries in the table 400. In various embodiments, this exceeds a "maximum matching" threshold.

It is understood that the percentage of match in some embodiments is not strictly based on an overlap or union (e.g., via Jaccard index) of matching entry candidate diagnoses. Rather, some embodiments adjust the matching percentage based on the weight values (e.g., as indicated in the table 400). For example, there may be a high percentage of match for most entries that only have a weight of [1] but low percentage of matching for a few entries that have a weight of [5]. In this situation, although most entries match, the weight signals that the corresponding medical presentation is not important for the corresponding candidate diagnosis. Rather, for a few important entries there are no matches but they are important for the corresponding candidate diagnosis. Accordingly, in this situation, certain embodiments reduce or otherwise modify the matching percentage directly proportional to the weight to make up for the bias of strict matching entries since those entries may be weighted high or low (may be important or not important for a corresponding candidate diagnosis).

As described herein, any suitable threshold can be used to determine the deviation score or match between determinations made for the candidate diagnosis (e.g., by the candidate diagnosis mapping component 202) and a validation score to indicate the accuracy of the candidate diagnosis for the same medical presentations (e.g., via the diagnosis validation component 204 of FIG. 2). For example, the following depicts the accuracy of a candidate diagnosis. If there is greater than or equal than a 70% match between an original candidate diagnosis and the candidate diagnosis determined by the decision statistic 607, then there is "maximal matching." Likewise, if there is between a greater than or equal to 40% and 70% match between an original candidate diagnosis and the candidate diagnosis determined by the decision statistic 607, then there is "moderate matching." Further, if there is less than or equal to a 40% match between an original candidate diagnosis and the candidate diagnosis determined by the decision statistic 607, then there is a "minimal matching."

The candidate diagnosis deviation alert(s) 611 represents visual and/or auditory alerts that are caused to be presented to a user device to notify a user based on deviation score generated by the candidate diagnosis deviation 609. For example, referring to the example above, for "maximum matching," some embodiments cause a green indicator to be displayed. For "moderate matching," some embodiments cause a yellow indicator to be displayed. For "minimal matching," some embodiments cause a red indicator to be displayed. Alternative or additional to color indicators that indicate the deviation score, other indicators can be used, such as natural language characters that state "maximal matching," for example, or the percentage of matching. In another example, indicators can be auditory beeps, noises, and/or smart speaker utterances that indicate the validation score. In another example, indicators can be a notification sent to a user device.

The feedback 613 represents any suitable user input feedback that the user can upload so that the machine learning model(s) 605 can continue to tune, train on, and modify its predictions based on the feedback (e.g., via reinforcement learning). Reinforcement learning, for example, is feedback-based learning based on positive or negative rewards given. In an illustrative example of the feedback 613, referring back to FIG. 4, some embodiments suggest the candidate diagnosis to be Cholelithiasis and present it to a computing device. However a user, such as a physician, may reject or refrain from selecting this diagnosis (e.g., a negative reward) and instead select another candidate diagnosis. In response to one or both of these user inputs, some embodiments send this information (e.g., automatically) to the machine learning model(s) 605 to learn that the listed medical presentation(s) listed are more indicative of the other candidate diagnosis, instead of Cholelithiasis. Alternatively or additionally, in response to receiving information, some embodiments flag or notify a device to change the weights and/or decision-making flags within the table 400.

In another illustrative example of the feedback 613, referring back to FIG. 4, although the decision statistic(s) 607 may suggest the candidate diagnosis to be Cholelithiasis, a user, such as a physician, may reject or refrain from selecting this diagnosis (e.g., a negative reward) and instead select another candidate diagnosis (e.g., a positive reward). In response to one or both of these user inputs, some embodiments send this information (e.g., automatically) to the machine learning model(s) 605 to learn that the listed medical presentation(s) listed are more indicative of the other candidate diagnosis, instead of Cholelithiasis.

Figure 7:
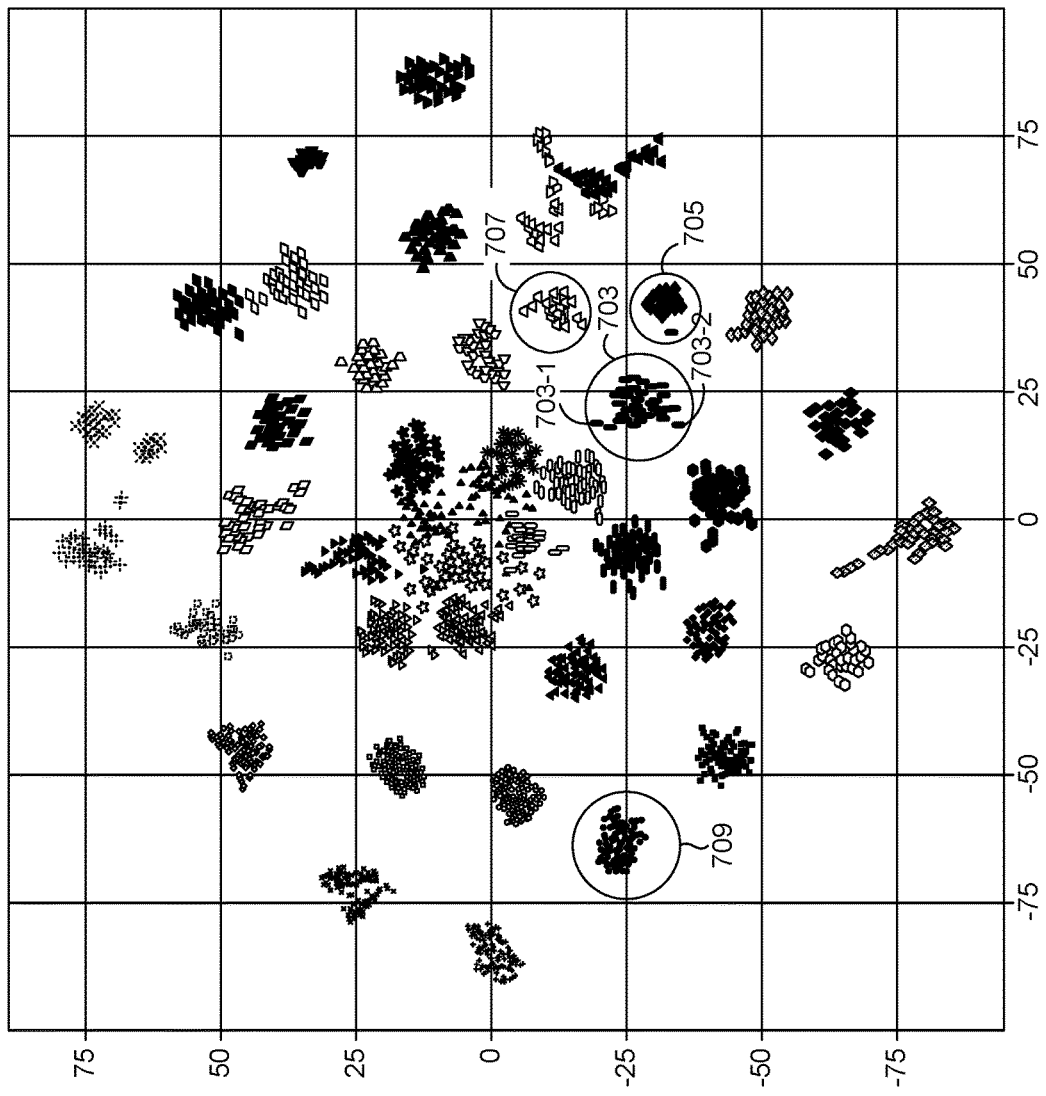
FIG. 7 is a schematic diagram of an example visualization of feature space that illustrates various feature vectors representing one or more training data inputs and/or runtime inputs, according to some embodiments of the present invention.

FIG. 7 is a schematic diagram of an example visualization of feature space 700 that illustrates various feature vectors representing one or more training data inputs (e.g., the training data input(s) 615) and/or runtime inputs (e.g., one or more of the runtime inputs 603), according to some embodiments. In some embodiments, the feature space 700 represents the functionality produced (or used) by the diagnosis validation component 204 and/or the machine learning model(s) 605 to determine what cluster (or class) a particular feature vector belongs to (e.g., whether a feature vector representing a patient's symptoms is mapped to a cluster representing a particular candidate diagnosis). In some embodiments, the feature space 700 represents any vector space described herein.

In some embodiments, the vector space 700 includes classes of data points (e.g., data point 703-1 and data point 703-2) representing individual feature vectors corresponding to specific training data inputs and/or runtime inputs. These data points are formed together to form a particular cluster (or class). For example, the data point 703-1 and data point 703-2 may have been clustered under 603 representing a "Cholelithiasis" candidate diagnosis (indicative that the feature values of the data points 703 are within a threshold distance to or similar to other trained data points). There are other clusters or classes, such as cluster 705 (e.g., "Ovarian Cyst") and the class 707 (e.g., "Fibromyalgia").

In an illustrative example of how the feature space 700 is used, embodiments may receive at least one of the runtime input(s) 603. Responsively, some embodiments run the runtime input(s) 603 through one or more machine learning models in order to weight features for the input(s) 603, after which a feature vector (e.g., representing the data point 703-1) is embedded in the feature space 700. The feature space 700 in various embodiments represents a multidimensional coordinate system where each feature is associated with one or more dimensions. For example, a first set of values in a vector may represent the medical presentations of a patient, where a first axis represents the first set of values and a second axis represents a second set of values of the same vector, which is the age of the patient. Each feature value within the feature vector may be summed or otherwise aggregated to arrive at a final coordinate point (e.g., the data point 703-2) within the feature space 700. Each of the data points within the cluster 703, for example, are within a feature similarity threshold and so they are close to each other (e.g., based on Euclidian distance) in the feature space 700. Responsive to the embedding of the feature vector in the feature space 700, embodiments cluster or classify the vectors. For example, if a first vector represents data point 703-1, then the classification that is nearest to the data point 703-1 is the "Cholelithiasis" Cluster or classification 603 indicative of the runtime input(s) 603 corresponding to or being indicative of Cholelithiasis.

The machine learning model(s) are able to cluster samples of new unseen inputs (e.g., any input received after training). In some embodiments, any input is represented by the median of its samples' embeddings as shown below:

$$C = \text{median}\{f_{embed}(S_i^j): I=1,2,\ldots,n\]$$

Where $f_{embed}$ is the output of the model, $S_i^j$ is the $i^{th}$ sample of the $j^{th}$ class. The prediction for any test sample X is given by:

$$Pred(X) = \arg\min_j \|C_j - f_{embed}(X)\|.$$

However, it is understood that median is just one way to represent an embedding. Some embodiments alternatively use other statistics like mean, Pth percentile, and the like.

FIG. 8 is a screenshot 800 of an example user interface, according to some embodiments. In some embodiments, the screenshot 800 represents a part of the consumer application 210 and/or what is caused to be presented by the presentation component 208 of FIG. 2. In some embodiments, the screenshot represents the output of the candidate diagnosis mapping component 202, where a candidate diagnosis—Cholelithiasis—is provided.

Various embodiments receive user input (e.g., from a patient or healthcare) of each medical presentation that a person experiences in the field 803. For example, after arriving at a doctor's appointment, a patient may describe the patient's chief complaint, after which the doctor may select or input the "problem type" 811 to be "chief complaint/RVF and may additionally input, into the field 803, all of complaints the patient is describing to her.

After listing all of the medical presentations in the field 803, the user may select the map button 815. In response to receiving an indication of the user selection of the map button 817, particular embodiments automatically receive the medical presentation data indicated in the field 803 and automatically map (e.g., as described with respect to the candidate diagnosis mapping component 202, the table 300 of FIG. 3 and/or the table 400 of FIG. 4) the medical presentation data in the field 803 to the "Cholelithiasis" candidate diagnosis indicated in the field 809, as well as the most common or known medical presentations associated with "Cholelithiasis" in the field 805. This mapping, as described with respect to the candidate diagnosis mapping component 202, the table 300 and/or the table 400 is based on a new set of rules not previously used by existing technologies.

The user may or may not agree with the candidate diagnosis as specified in the field 809. Accordingly, the user may either select the "OK" button 813 or the "cancel" button 817. In response receiving an indication of the selection of the "OK" button 813, particular embodiments infer that the user is confirming or otherwise agreeing with the candidate diagnosis suggestion in the field 809. In some embodiments, this confirmation activates a value function in reinforcement learning to inform an agent about the maximum reward that the agent receives or otherwise provides the feedback 613 as described with respect to FIG. 6. In response receiving an indication of the selection of the "Cancel" button 817, particular embodiments infer that the user is rejecting or otherwise disagreeing with the candidate diagnosis suggestion in the field 809. In some embodiments, this rejection activates the feedback 613 as described with respect to FIG. 6. In response to receiving of the indication of the "Cancel" button 817, some embodiments automatically generate a list of other potential candidate diagnoses as determined, for example, for each entry (medical presentation) of the table 400.

The screenshot 800 illustrates an improvement over existing user interfaces and technologies by automating the diagnosis in the field 809 based on new rules and giving a practitioner more control (e.g., via the feedback 613 and the cancel button 817) over candidate diagnoses, since existing AI technologies, for example, give practitioners little control over candidate diagnoses.

FIG. 9 is a screenshot 900 of an example user interface, according to some embodiments. In some embodiments, the screenshot 900 represents a part of the consumer application 210 and/or what is caused to be presented by the presentation component 208 of FIG. 2. In some embodiments, the screenshot 900 represents the output of the candidate diagnosis mapping component 202, where a candidate diagnosis—Jaundice—is provided. In some embodiments, the screenshot 900 represents identical functionality and features relative to the screenshot 800 of FIG. 8, except that the inputted medical presentation data is different, as well as the mapped candidate diagnosis, and the "problem type" is "Codified Presenting Problem."

Figure 10B:
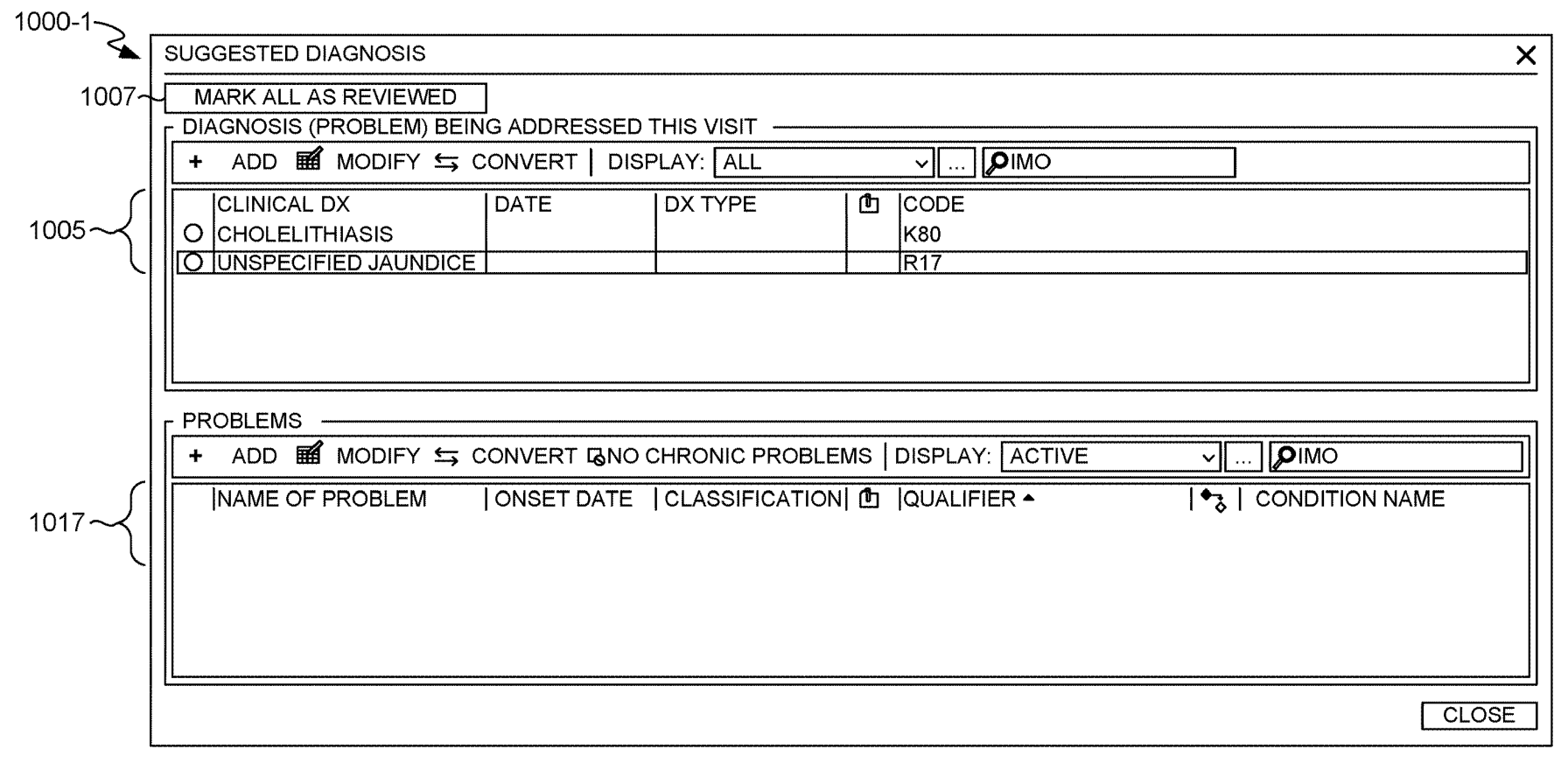

FIGS. 10A and 10B are screenshots 1000 and 1000-1 of example user interfaces, according to some embodiments. In some embodiments, the screenshot 1000 and 1000-1 represent a part of the consumer application 210 and/or what is caused to be presented by the presentation component 208 of FIG. 2. In some embodiments, the screenshot 1000-1 represents the output of the candidate diagnosis mapping component 202.

Various embodiments receive user input (e.g., from a patient or healthcare) of each medical presentation that a person experiences in the field 1003. After listing all of the medical presentations in the field 1003, particular embodiments automatically receive the medical presentation data indicated in the field 1003 and automatically map (e.g., as described with respect to the candidate diagnosis mapping component 202, the table 300 of FIG. 3 and/or the table 400 of FIG. 4) the medical presentation data in the field 1003 to the "Cholelithiasis" candidate diagnosis and/or the "unspecified Jaundice" indicated in the field 809. This mapping, as described with respect to the candidate diagnosis mapping component 202, the table 300 and/or the table 400, is based on a new set of rules not previously used by existing technologies. The field 1017 is configured to receive user input so that a user can input additional medical presentations if needed and the suggested candidate diagnosis can be modified. In some embodiments, in response to receiving an indication of the selection of the button 1007, the information within the screenshot 1000-1 and/or 1000 is used for continued learning or tuning of a machine learning model (e.g., via the feedback 613).

Some embodiments automatically cause presentation of the screenshot 1000-1 in response to receiving the presentation data in the field 1003, which improves existing technologies that require extensive drilling down, browsing, or other user input, thereby improving the user experience.

Figure 10C:
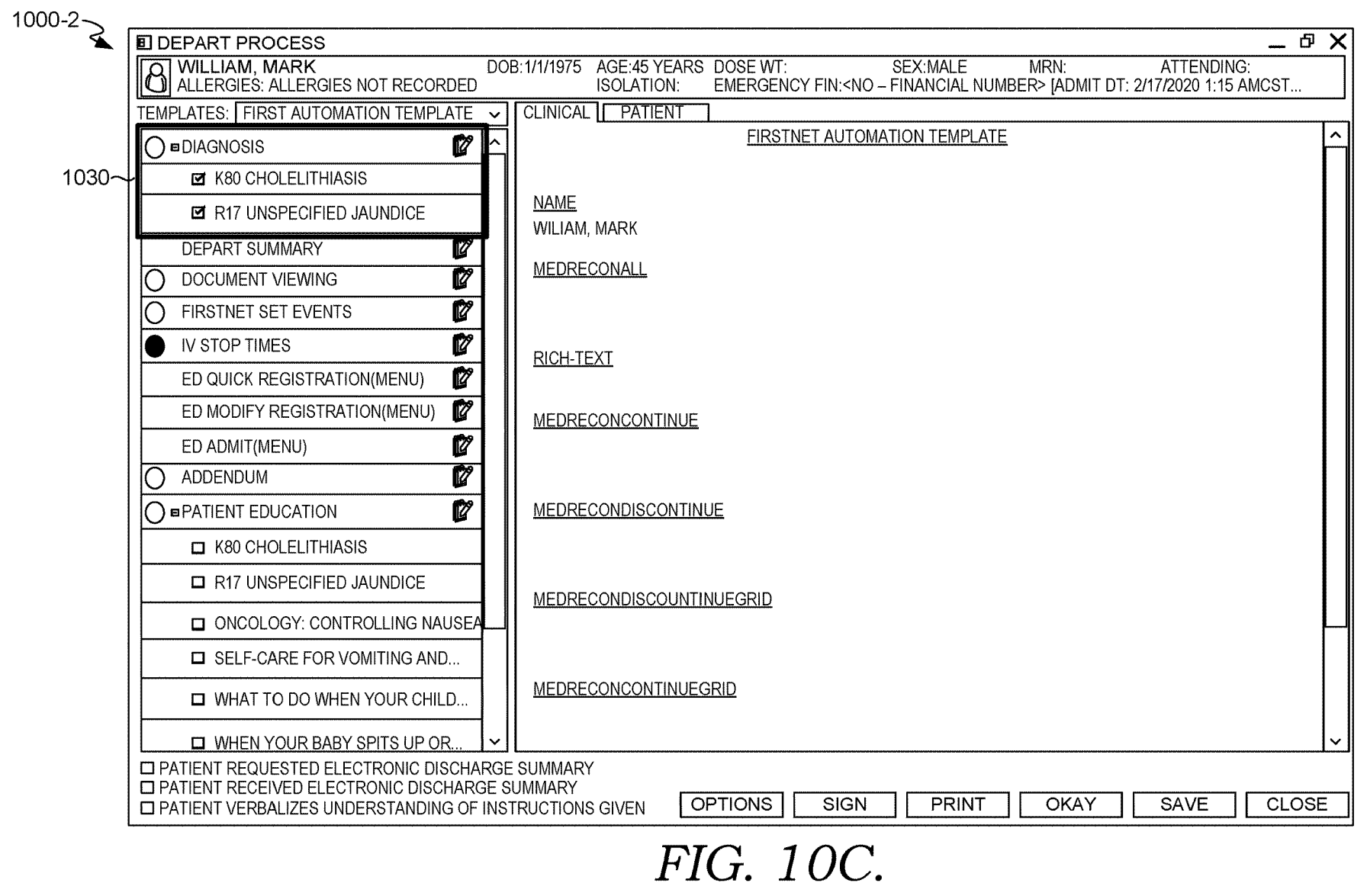

FIG. 10C illustrates a screenshot 1000-2 of an example user interface, according to some embodiments. In some embodiments, the screenshot 1000-2 represents a part of the consumer application 210 and/or what is caused to be presented by the presentation component 208 of FIG. 2. In some embodiments, the screenshot 1000-2 illustrates what is output or caused to be displayed (e.g., automatically) in response to the display of the screenshot 1000-1 and/or a selection of "Cholelithiasis" or "unspecified jaundice" in the screenshot 1000-1 of FIG. 10B. For example, the information in the UI element 1030 is automatically populated in response to one of these selections.

In some embodiments, FIG. 10C illustrates an automated template that is automatically populated, in natural language, based on one or more inputs. For example, the name under the "name" header, a name can be populated, as well as information under a "diagnosis" header, such as "Cholelithiasis" or "unspecified jaundice." In some embodiments, the automation template is populated based on selections, such as the "diagnosis" field in the screenshot 10002. In some embodiments, the automation template corresponds to doctor's notes, chart information, intake information, and/or any other suitable medical documentation.

FIG. 11 illustrates a screenshot 1100 of an example user interface, according to some embodiments. In some embodiments, the screenshot 1100 represents a part of the consumer application 210 and/or what is caused to be presented by the presentation component 208 of FIG. 2. In some embodiments, the screenshot 1100 represents the screenshot 1000-1, except that diagnosis deviation alert indicator 1103 has been provided (e.g., in response to the diagnosis validation component 204 performing its functionality)

FIG. 11 illustrates how a user interface appears after a validation score has been generated to indicate an accuracy of a candidate diagnosis, according to some embodiments. Specifically, the deviation alert indicator 1103 (e.g., the circle that is a green color) is caused to be presented, which indicates a validation score. In some embodiments, the deviation alert indicator 1103 is caused to be displayed via the candidate diagnosis deviation alert(s) 611 as described with respect to FIG. 6 and/or in response to the diagnosis validation component 204 of FIG. 2 performing its functionality. In some embodiments the deviation alert indicator 1103 is caused to be additionally or presented at the screenshot 800, 900, 1000, and/or 1000-2 of FIG. 8, FIG. 9, FIG. 10A, and FIG. 10B respectively.

By providing the deviation alert indicator 1103 to these screenshots or other landing pages, this reduces the amount of manual user entry to confirm diagnosis, as well as reduces the amount of drilling, browsing, or selecting a user must make to confirm a diagnosis, which improves existing UIs and the user experience, as described herein. Further, the deviation alert indicators or other indicators of the validation score as described herein help improve the user experience because users, such as healthcare practitioners, are better able to gauge whether more mapping or other functionality needs to be performed at the user interface. For example, if the indicator is green, which may indicate there is a high validation score, then this indicates to the user that she does not need to keep mapping or otherwise inputting additional diagnosis or other information, since the original candidate diagnosis suggestion is probably accurate.

Figure 12:
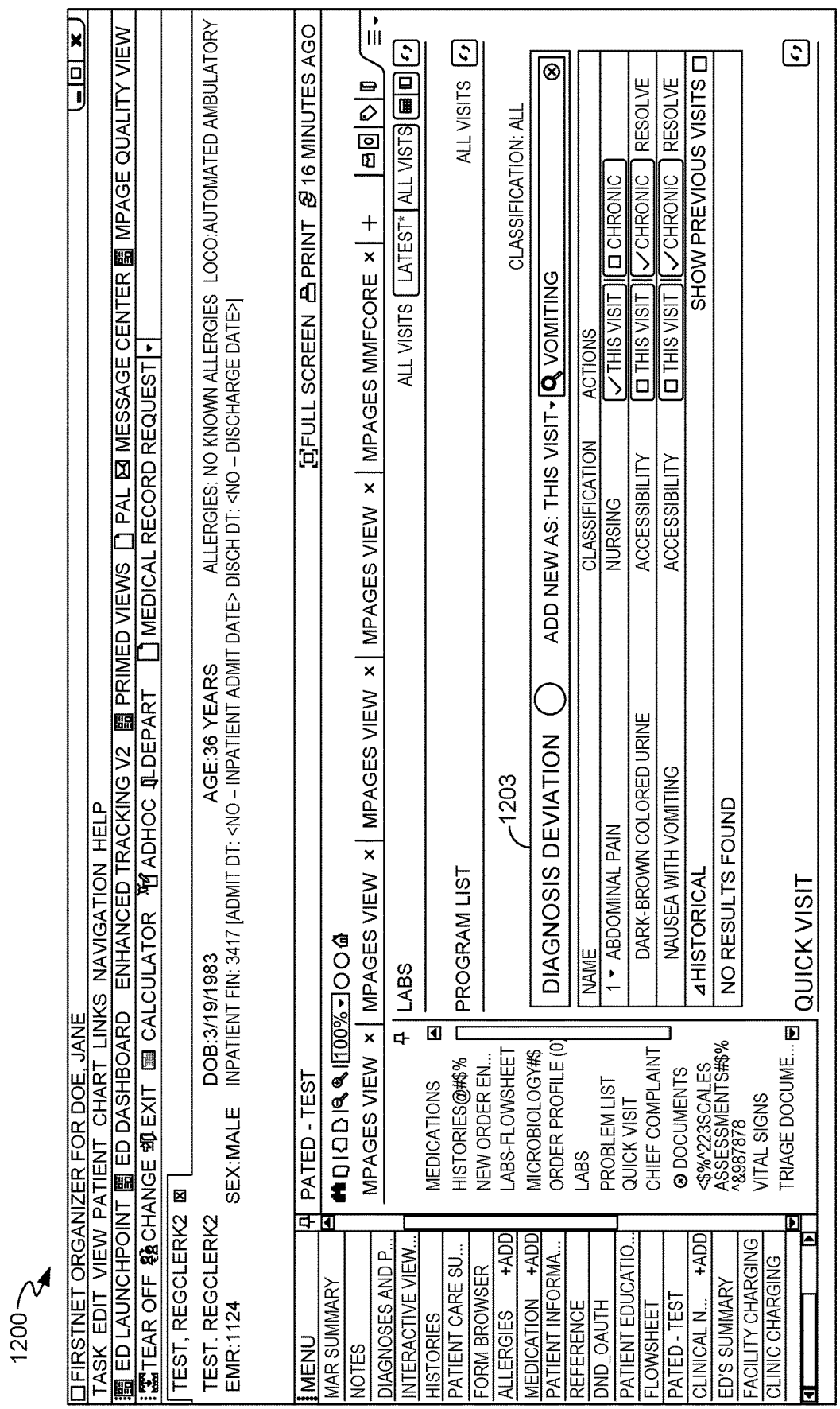
FIG. 12 is a screenshot of an example user interface, according to some embodiments of the present invention.

FIG. 12 illustrates a screenshot 1200 of an example user interface, according to some embodiments. In some embodiments, the screenshot 1200 represents a part of the consumer application 210 and/or what is caused to be presented by the presentation component 208 of FIG. 2.

FIG. 12 illustrates how a user interface appears after a validation score has been generated to indicate an accuracy of a candidate diagnosis according to some embodiments. Specifically, the deviation alert indicator 1203 (e.g., the circle that is a red color) is caused to be presented, which indicates a validation score. In some embodiments, the deviation alert indicator 1203 is caused to be displayed via the candidate diagnosis deviation alert(s) 611 as described with respect to FIG. 6 and/or in response to the diagnosis validation component 204 of FIG. 2 performing its functionality.

Figure 13:
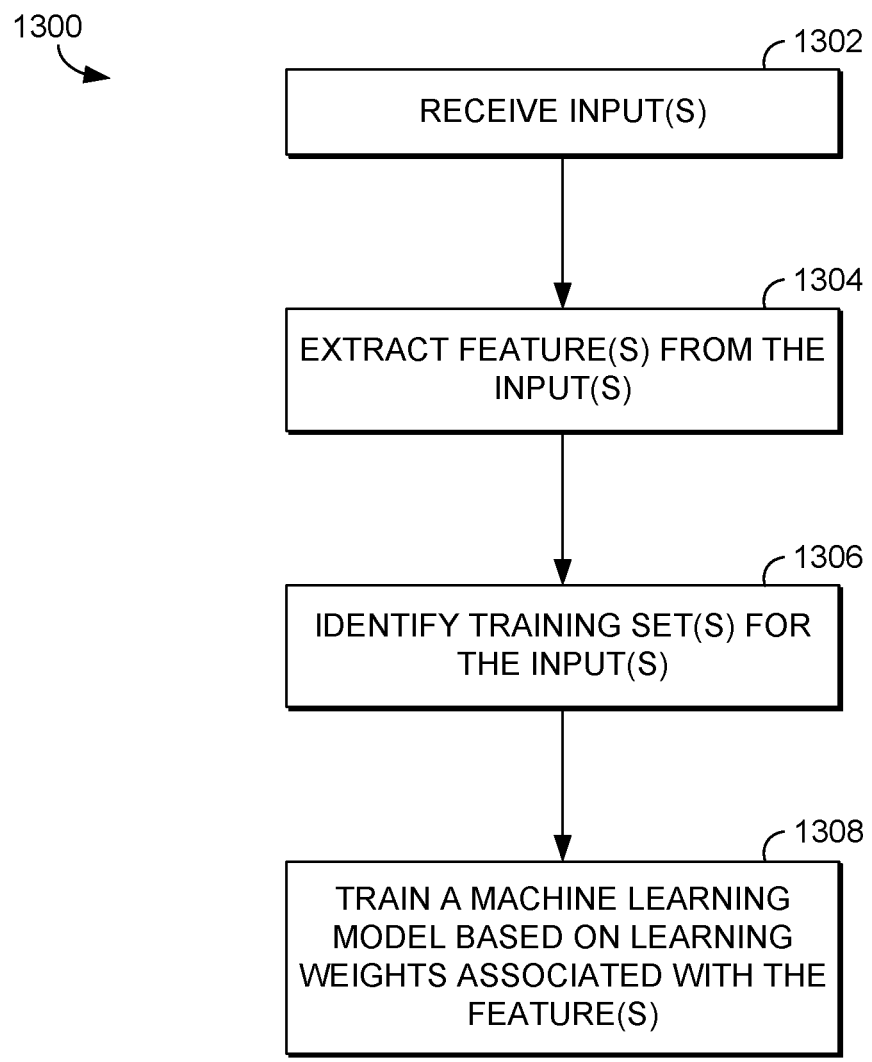
FIG. 13 is a flow diagram of an example process for training a machine learning model, according to some embodiments of the present invention.

FIG. 13 is a flow diagram of an example process 1300 for training a machine learning model, according to some embodiments. In some embodiments, the process 1300 is performed to train the one or more machine learning models 605 of FIG. 6.

The process 1300 (and/or any of the functionality described herein) may be performed by processing logic that comprises hardware (e.g., circuitry, dedicated logic, programmable logic, microcode, etc.), software (e.g., instructions run on a processor to perform hardware simulation), firmware, or a combination thereof. Although particular blocks described in this disclosure are referenced in a particular order at a particular quantity, it is understood that any block may occur substantially parallel with or before or after any other block. Further, more (or fewer) blocks may exist than illustrated. Added blocks may include blocks that embody any functionality described herein (e.g., as described with respect to FIG. 1 through FIG. 12). The computer-implemented method, the system (that includes at least one computing device having at least one processor and at least one computer readable storage medium), and/or the computer readable medium as described herein may perform or be caused to perform the process 1300 or any other functionality described herein.

Per block 1302, one or more inputs (e.g., the training data input(s) 615 of FIG. 6) are received. In some embodiments, the one or more inputs have been labelled or classified according to features within the inputs prior to training. For example, some embodiments are supervised and may receive a user input label of "Ovarian Cycst" or "Jaundice" indicative of a data source (e.g., of symptoms) being indicative of these labels. Alternatively, in some embodiments the one or more inputs are not labeled or have no classification prior to training, such as in some unsupervised machine learning contexts.

Per block 1304, particular embodiments extract one or more features from each of the one or more inputs. For example, some embodiments extract words of documents, such as books, medical charts, family history, social history, procedure history, and the like for multiple (e.g., anonymized) patients.

Per block 1306, one or more training sets are identified for the input(s). For example, in a supervised context where inputs are labelled, inputs with the same label are identified in preparation for training. In an illustrative example, pairs of inputs that have the same label can be paired, as well as pairs of inputs that have differing labels can be paired. In unsupervised context where inputs are not labeled, any input can be paired with any other arbitrary or randomly selected other input.

Per block 1308, a machine learning model (e.g., a deep learning model) is trained based at least in part on learning weights associated with the extracted features. For example, the machine learning model may ingest several data sources that each describe symptoms and signs for "Ovarian Cyst." In each of these data sources, there may be a common first symptom associated with Ovarian Cyst. However, a second symptom may only be associated with Ovarian Cyst in only a few of the data sources. Accordingly, embodiments can weight the first symptom higher (e.g., activate a neural node close to the value of 1) and weight the second symptom lower (e.g., inhibit another neural node close to the value of 0).

In some embodiments, pairs of same labeled inputs (e.g., different books with the same labeled diagnosis) and dissimilar labelled inputs (e.g., different books with different labeled diagnoses) are processed or run through a deep learning model by comparing the associated features and mapping it in feature space. And based at least in part on the processing, weights associated with the deep learning model can be adjusted to indicate the importance of the extracted featured for prediction or classification. In some embodiments, as described herein, the adjusting includes activating, strengthening, or inactivating a neuron or node in a neural network. In some embodiments, the adjusting includes changing an embedding in feature space of a feature vector representing the image feature(s). For example, after a first round or epochs of training, it may be unknown which of the extracted features are important for taking on a certain classification or prediction. Accordingly, each feature may take on equal weight (or close to equal weight within a threshold, such as a 2% changed weight) such that all of the input feature vectors are substantially close or within a distance threshold in feature space. However, after several rounds of training or any threshold quantity of training, these same feature vectors may adjust or change distances from each other based on the feature value similarity. The more features of two feature vectors that match or are within a threshold value, the closer the two feature vectors are to each other, whereas when features do not match or are not within a threshold value, the further away the two feature vectors are from each other. Accordingly, for example, a trained embedding may look similar to the feature space 700 of FIG. 7.

Figure 14:
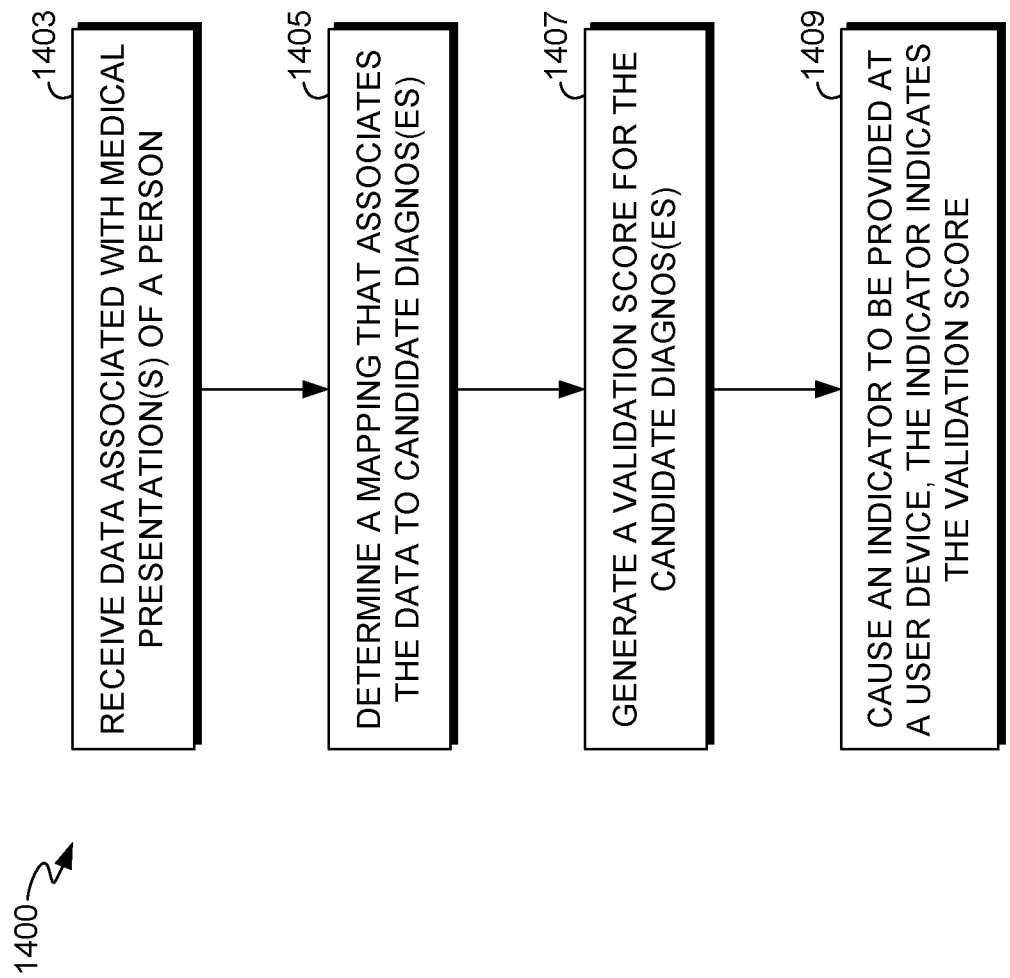
FIG. 14 is a flow diagram of an example process for generating a validation score that indicates an accuracy of a candidate diagnosis, according to some embodiments of the present invention.

FIG. 14 is a flow diagram of an example process 1400 for generating a validation score that indicates an accuracy of a candidate diagnosis, according to some embodiments. Per block 1403, particular embodiments receive data associated with one or more medical presentations of a person. For example, a patient may arrive in ED/hospital. An ED Clerk/Nurse Quick Registers the Patient and documents the Chief Complain/Reason for visit. The Triage Nurse may then perform initial assessment and document the presenting problems, observation, symptoms, vital signs, etc. Accordingly, referring back to FIG. 9, particular embodiments receive the data (e.g., that the ED Clerk/Nurse has documented) in the field 803 in response to receiving an indication that the "map" button 815 was selected (e.g., by the ED Clerk/Nurse).

In some embodiments, the one or more medical presentations of the person is at least one of: data that specifies the symptom(s) of a person, data that specifies a chief complaint of the person, data that specifies a reason for visit by the person to a healthcare practitioner, sign(s) of the person, and/or presenting problems of the person.

Per block 1405, some embodiments determine a mapping that associates the data to one or more candidate diagnosis. The one or more candidate diagnoses correspond to one or more possible medical conditions associated with the person. Examples of this mapping include functionality as described with respect to the candidate diagnosis mapping component 202 of FIG. 2, the table 300 of FIG. 3, the table 400 of FIG. 4, and/or the screenshot 900 of FIG. 9. In some embodiments, this mapping can be generated (e.g., a data structure can be built or programmatically called) or analyzed (e.g., looked up), alternative or in addition to being "determined," which can include the terms "generate" and "analyze."

In some embodiments, the determining of the mapping is based on one or more predetermined rules and/or a first set of features. For example, the one or more "predetermined rules" may refer to the inclusion and/or exclusion criteria as described with respect to FIG. 4 and FIG. 5. Alternatively or additionally, the predetermined rules may refer to any other functionality as described with respect to FIG. 3, FIG. 4, and/or FIG. 5, such as the decision-making flags, the weights, and the like.

In some embodiments, the "first set of features" include at least one attribute of a group of attributes, such as the age of the person, gender of the person, race of the person, the procedure history of the person, and/or the data received at block 1403. Examples of the first set of attributes are indicated in the table 300 of FIG. 3 and/or the table 400 of FIG. 4.

In some embodiments, the one or more possible medical conditions associated with the person includes one or more possible diseases the person has and/or any other medical condition or state, such as a particular: sickness, viral infection, bacterial infection, deformity, syndrome, ailment, or the like.

In some embodiments, the determination of the mapping per block 1405, the generation of the validation score per block 1407, and/or the causing of the indicator to be provided per block 1409 occurs automatically (e.g., via new rules) without user input. This improves existing technologies that require manual and tedious user input.

Per block 1407, some embodiments generate a validation score for the one or more candidate diagnoses. The validation score indicates an accuracy of the candidate diagnosis. Examples of the validation score are described with respect to the diagnosis validation component 204 of FIG. 2, the candidate diagnosis deviation 609, and the diagnosis deviation alert 1103 of FIG. 11.

Some embodiments receive, via a user interface of a computing device, an indication of a selection associated with at least a first candidate diagnosis of the one or more candidate diagnoses and in response to the receiving of this indication of selection, particular embodiments perform the generation of the validation score at block 1407. For example, referring back to FIG. 8, in response to receiving an indication of the selection of the "OK" button 813, particular embodiments generate the validation score (e.g., and also provide the diagnosis deviation alert 1103 to the screenshot 800). The selection or "OK" button 813 is associated with the "Cholelithiasis" candidate diagnosis, as indicated in the field 809.

In some embodiments, the generating of the validation score is based on a second set of features associated with the person (e.g., which may be the same as the first set of features). In some embodiments, the second set of features include at least one feature that is different than the first set of features. For example, referring back to FIG. 3, the first set of features may include all the features in the table 300, such as the gender, age, race, procedure history, social history, and family of a person. However, the second set of features may include additional features not included in the table 300, such as any different feature included in the runtime input(s) 603 (e.g., sensor data, third party source(s), user device data, etc.). In some embodiments, the second set of features are used as input into one or more machine learning models for the generation of the validation score. For example, referring back to FIG. 6, the runtime input(s) 603 are processed through the one or more machine learning model(s) 605 to generate a decision statistic 607 and then validation score at 609.

The validation score can refer to any integer (or set of integers), matching percentage, cardinality measure (e.g., whether a candidate diagnosis is "accurate" or "not accurate"), Boolean value (e.g., TRUE or FALSE), floating point value, and/or any other real number value. For example, in some embodiments, the validation score indicates that: the first candidate diagnosis for the one or more medical presentations is maximally accurate over a threshold (e.g., a percent match), the first candidate diagnosis for the one or more medical presentations is moderately accurate between a second threshold and the first threshold, or the first candidate diagnosis for the one or more medical presentations is minimally accurate under the second threshold. Examples of this are described above with respect to the candidate diagnosis deviation 609 and the diagnosis validation component 204.

Per block 1409, some embodiments cause an indicator to be provided at a user device, where the indicator indicates the validation score. For example, this is described with respect to the candidate diagnosis deviation alert(s) 611 of FIG. 6 and the diagnosis deviation alert 1103 of FIG. 11. In some embodiments, block 1409 includes causing the indicator to be displayed at a user interface (or generating a user interface) in response to the generating of the validation score at block 1407, as described, for example, by the diagnosis deviation alert 1103 of FIG. 11. For example, the server(s) 102 of FIG. 1 may cause the remote computer 108 to display a deviation alert. Alternatively, block 1409 may include causing an auditory indicator (e.g., an utterance) to be provided at a virtual assistant. For example, a server may send a control signal to a smart speaker, thereby causing the smart speaker to utter the validation score.

In some embodiments, the indicator displayed to the user interface indicates one of: the maximally accurate validation score (e.g., via a green colored icon), the moderately accurate validation score (e.g., via a yellow colored icon), and the minimally accurate validation score (e.g., via a red colored icon), as described, for example, with respect to the candidate diagnosis deviation alert(s) 611.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

Figure 15:
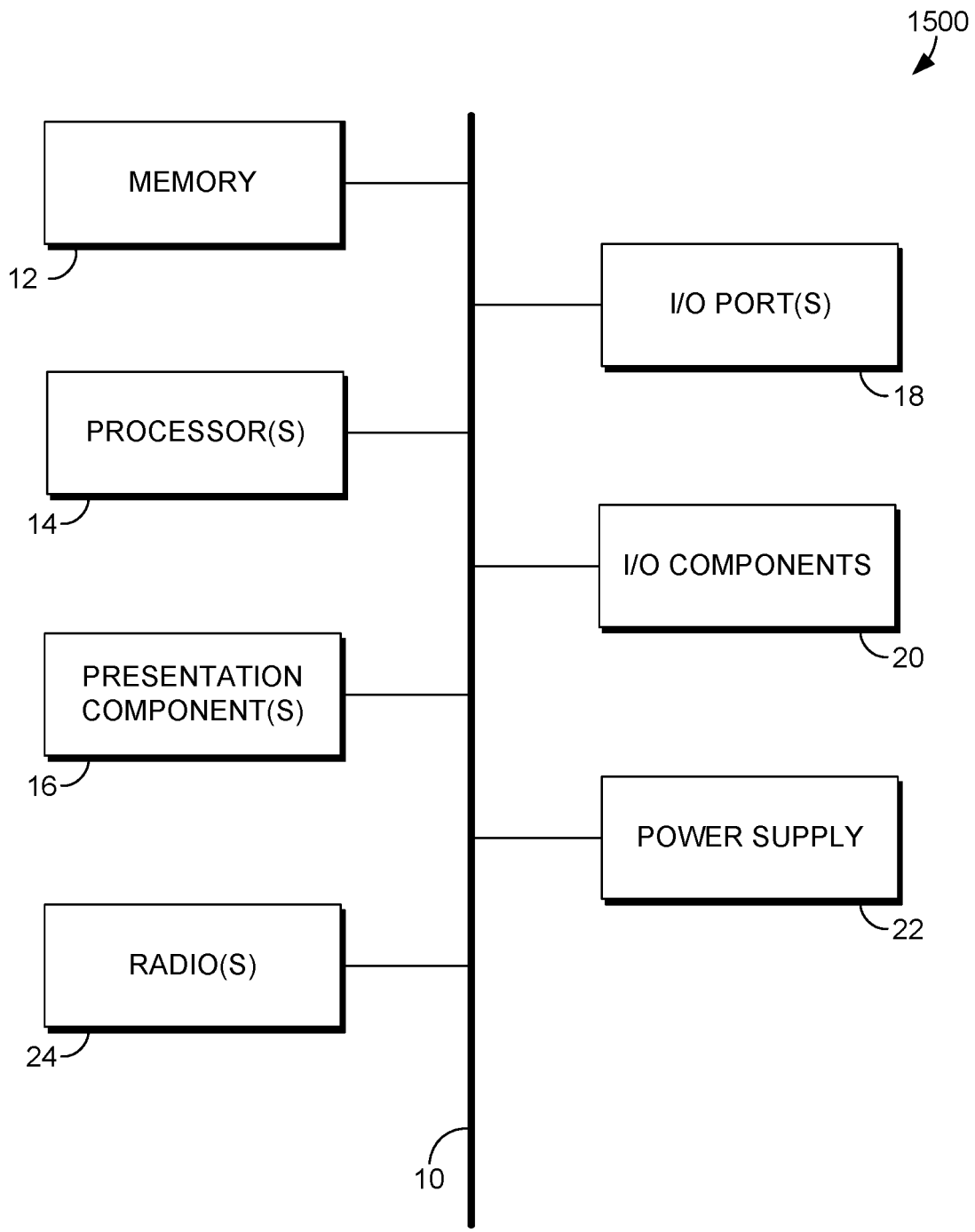
FIG. 15 is a block diagram of a computing device in which aspects of the present disclosure are implemented within, according to some embodiments of the present invention.

Having described embodiments of the present invention, an exemplary operating environment in which embodiments of the present invention may be implemented is described below in order to provide a general context for various aspects of the present invention. Referring initially to FIG. 15 in particular, an exemplary operating environment for implementing embodiments of the present invention is shown and designated generally as computing device 1500. Computing device 1500 is but one example of a suitable computing environment and is not intended to suggest any limitation as to the scope of use or functionality of the invention. Neither should the computing device 1500 be interpreted as having any dependency or requirement relating to any one or combination of components illustrated.

Looking now to FIG. 15, computing device 1500 includes a bus 10 that directly or indirectly couples the following devices: memory 12, one or more processors 14, one or more presentation components 16, input/output (I/O) ports 18, input/output components 20, and an illustrative power supply 22. Bus 10 represents what may be one or more busses (such as an address bus, data bus, or combination thereof). Although the various blocks of FIG. 15 are shown with lines for the sake of clarity, in reality, delineating various components is not so clear, and metaphorically, the lines would more accurately be grey and fuzzy. For example, one may consider a presentation component such as a display device to be an I/O component. Also, processors have memory. The inventor recognizes that such is the nature of the art, and reiterates that the diagram of FIG. 15 is merely illustrative of an exemplary computing device that can be used in connection with one or more embodiments of the present invention. Distinction is not made between such categories as "workstation," "server," "laptop," "hand-held device," etc., as all are contemplated within the scope of FIG. 15 and reference to "computing device" or "user device."

Computing device 1500 typically includes a variety of computer-readable media. Computer-readable media can be any available media that can be accessed by computing device 1500 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 1500. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media. In various embodiments, the computing device 1500 represents the remote computers 108 and/or the one or more servers 102 and vice versa.

Memory 12 includes computer-storage media in the form of volatile and/or nonvolatile memory. The memory may be removable, non-removable, or a combination thereof. Exemplary hardware devices include solid-state memory, hard drives, optical-disc drives, etc. Computing device 1500 includes one or more processors that read data from various entities such as memory 12 or I/O components 20. Presentation component(s) 16 present data indications to a user or other device. Exemplary presentation components include a display device, speaker, printing component, vibrating component, etc. In some embodiments, the memory includes program instructions that, when executed by one or more processors, cause the one or more processors to perform any functionality described herein, such as the process 1400 of FIG. 14.

I/O ports 18 allow computing device 1500 to be logically coupled to other devices including I/O components 20, some of which may be built in. Illustrative components include a microphone, joystick, game pad, satellite dish, scanner, printer, wireless device, etc. The I/O components 20 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing device 1500. The computing device 1500 may be equipped with depth cameras, such as stereoscopic camera systems, infrared camera systems, RGB camera systems, touchscreen technology, and combinations of these, for gesture detection and recognition. Additionally, the computing device 1500 may be equipped with accelerometers or gyroscopes that enable detection of motion. The output of the accelerometers or gyroscopes may be provided to the display of the computing device 1500 to render immersive augmented reality or virtual reality.

From the foregoing, it will be seen that this invention is one well adapted to attain all the ends and objects set forth above, together with other advantages which are obvious and inherent to the system and method. It will be understood that certain features and sub combinations are of utility and may be employed without reference to other features and sub combinations. This is contemplated by and is within the scope of the claims.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

What is claimed is:

1. A computer-implemented method, comprising:
   receiving data associated with one or more medical presentations of a person;
   analyzing a mapping that associates the data to one or more candidate diagnoses, the one or more candidate diagnoses corresponding to one or more possible medical conditions associated with the person;
   generating a validation score for a first candidate diagnosis, of the one or more candidate diagnoses, based on a set of features associated with the person and based further on a machine-learning electronic model, wherein:
   (a) the machine-learning electronic model is trained by inputting, to the machine-learning electronic model, vectors of information corresponding to instances of the set of features associated with people, wherein training the machine-learning electronic model is based at least in part on learning weights associated with the set of features and converting or encoding inputs into corresponding feature vectors,
   (b) the generating comprises applying, to the trained machine-learning electronic model, to data associated with at least a portion of the set of features to facilitate the generation of the validation score, and
   (c) the validation score indicates an accuracy of the first candidate diagnosis; and
   at least partially in response to the generating of the validation score, causing an indicator to be provided at a user device, the indicator indicates the validation score,
   wherein the analyzing of the mapping, the generating of the validation score, and the causing of the indicator to be displayed occurs automatically without user input.

2. The method of claim 1, wherein the one or more possible medical conditions associated with the person includes one or more possible diseases that the person has.

3. The method of claim 2, wherein the data associated with the one or more medical presentations of the person is at least one data set of a group of data sets consisting of: data that specifies presentations of the person, data that specifies signs of the person, data that specifies a chief complaint of the person, data that specifies a reason for a visit by the person to a healthcare practitioner, and presenting problems of the person.

4. The method of claim 1, wherein the set of features include at least one attribute of a group of attributes consisting of: age of the person, gender of the person, race of the person, and procedure history of the person.

5. The method of claim 4, wherein a first attribute value of a first attribute associated with the group of attributes is determined based on a second attribute value of a second attribute associated with the group of attributes.

6. The method of claim 1, wherein the set of features include at least one attribute of a group of attributes consisting of: a medical history of the person, a medical history of a family of the person, and a social history of the person.

7. The method of claim 6, wherein the set of features are input into the trained machine-learning electronic model for the generation of the validation score.

8. The method of claim 1, wherein the validation score indicates that: the first candidate diagnosis for the one or more medical presentations is maximally accurate over a first threshold, the first candidate diagnosis for the one or more medical presentations is moderately accurate between a second threshold and the first threshold, or the first candidate diagnosis for the one or more medical presentations is minimally accurate under the second threshold.

9. The method of claim 8, wherein the indicator is displayed at a user interface and indicates one of: a maximally accurate validation score, a moderately accurate validation score, and a minimally accurate validation score.

10. The method of claim 1, further comprising training the machine-learning electronic model based at least in part on iteratively learning the weights associated with the set of features.

11. The method of claim 1, further comprising applying the machine-learning electronic model to data elements associated with the set of features to facilitate the generation of the validation score.

12. The method of claim 1, further comprising updating the training of the machine-learning electronic model based on one or more of: (i) additional data or (ii) additional features associated with the data or with the additional data.

13. The method of claim 1, wherein the analyzing of the mapping, the generating of the validation score, and the causing of the indicator to be displayed occur automatically and sequentially.

14. The method of claim 1, wherein the training is based at least in part on a process selected from a group comprising supervised machine learning, reinforcement machine learning, and unsupervised machine learning.

15. One or more non-transitory media having instructions that, when executed by one or more processors, cause the one or more processors to facilitate a plurality of operations, the operations comprising:

receiving data associated with one or more medical presentations of a person;

analyzing a mapping that associates the data to one or more candidate diagnoses, the one or more candidate diagnoses corresponding to one or more possible medical conditions associated with the person;

generating a validation score for a first candidate diagnosis, of the one or more candidate diagnoses, based on a set of features associated with the person and based further on a machine-learning electronic model, wherein:

(a) the machine-learning electronic model is trained by inputting, to the machine-learning electronic model, vectors of information corresponding to instances of the set of features associated with people, wherein training the machine-learning electronic model is based at least in part on learning weights associated with the set of features and converting or encoding inputs into corresponding feature vectors, (b) the generating comprises applying, to the trained machine-learning electronic model, to data associated with at least a portion of the set of features to facilitate the generation of the validation score, and (c) the validation score indicates an accuracy of the first candidate diagnosis; and at least partially in response to the generating of the validation score, causing an indicator to be provided at a user device, the indicator indicates the validation score, wherein the analyzing of the mapping, the generating of the validation score, and the causing of the indicator to be displayed occurs automatically without user input.

16. The one or more non-transitory media of claim 15, wherein the mapping is generated based at least in part on a first set of features, and wherein a second set of features includes the first set of features.

17. The one or more non-transitory media of claim 15, wherein the data associated with the one or more medical presentations of the person is at least one data set of a group of data sets consisting of: data that specifies a chief complaint of the person, data that specifies a reason for a visit by the person to a healthcare practitioner, and presenting problems of the person.

18. The one or more non-transitory media of claim 15, wherein the mapping is generated based on at least one attribute of a group of attributes consisting of: age of the person, gender of the person, race of the person, and procedure history of the person.

19. The one or more non-transitory media of claim 15, wherein the mapping is generated based on one or more predetermined rules.

20. The one or more non-transitory media of claim 15, wherein the set of features include at least one attribute of a group of attributes consisting of: a medical history of the person, a medical history of a family of the person, and a social history of the person.

21. The one or more non-transitory media of claim 15, wherein the set of features are input into the machine-learning electronic model for the generation of the validation score.

22. The one or more non-transitory media of claim 15, wherein the validation score indicates that: the first candidate diagnosis for the one or more medical presentations is maximally accurate over a first threshold, the first candidate diagnosis for the one or more medical presentations is moderately accurate between a second threshold and the first threshold, or the first candidate diagnosis for the one or more medical presentations is minimally accurate under the second threshold.

23. The one or more non-transitory media of claim 22, wherein the indicator is displayed at a user interface and indicates one of: a maximally accurate validation score, a moderately accurate validation score, and a minimally accurate validation score.

24. The one or more non-transitory media of claim 15, wherein the machine-learning electronic model comprises a deep learning model.

25. A system having one or more processors configured to perform a plurality of operations, the operations comprising:

receiving data associated with one or more medical presentations of a person;

analyzing a mapping that associates the data to one or more candidate diagnoses, the one or more candidate diagnoses corresponding to one or more possible medical conditions associated with the person;

generating a validation score for a first candidate diagnosis, of the one or more candidate diagnoses, based on a set of features associated with the person and based further on a machine-learning electronic model, wherein:

(a) the machine-learning electronic model is trained by inputting, to the machine-learning electronic model, vectors of information corresponding to instances of the set of features associated people, wherein training the machine-learning electronic model is based at least in part on learning weights associated with the set of features and converting or encoding inputs into corresponding feature vectors, (b) the generating comprises applying, to the trained machine-learning electronic model, to data associated with at least a portion of the set of features to facilitate the generation of the validation score, and (c) the validation score indicates an accuracy of the first candidate diagnosis; and at least partially in response to the generating of the validation score, causing an indicator to be provided at a user device, the indicator indicates the validation score, wherein the analyzing of the mapping, the generating of the validation score, and the causing of the indicator to be displayed occurs automatically without user input.

* * * * *